US010478456B2

(12) United States Patent
Ankersmit

(10) Patent No.: US 10,478,456 B2
(45) Date of Patent: Nov. 19, 2019

(54) PHARMACEUTICAL PREPARATION

(75) Inventor: Hendrik Jan Ankersmit, Vienna (AT)

(73) Assignee: APOSCIENCE AG, Vienna (AT)

( * ) Notice: Subject to any disclaimer, the term of this patent is extended or adjusted under 35 U.S.C. 154(b) by 147 days.

(21) Appl. No.: 13/140,120

(22) PCT Filed: Dec. 18, 2009

(86) PCT No.: PCT/EP2009/067536
§ 371 (c)(1),
(2), (4) Date: Jun. 16, 2011

(87) PCT Pub. No.: WO2010/070105
PCT Pub. Date: Jun. 24, 2010

(65) Prior Publication Data
US 2011/0250190 A1    Oct. 13, 2011

(30) Foreign Application Priority Data
Dec. 18, 2008    (EP) ..................... 08450199

(51) Int. Cl.
| A61K 35/14 | (2015.01) |
| A61P 9/10 | (2006.01) |
| A61P 19/00 | (2006.01) |
| A61P 11/00 | (2006.01) |
| A61P 37/06 | (2006.01) |
| A61P 29/00 | (2006.01) |
| A61P 1/00 | (2006.01) |
| A61K 35/17 | (2015.01) |

(52) U.S. Cl.
CPC .................... *A61K 35/17* (2013.01)

(58) Field of Classification Search
CPC ............. A61K 38/00; A61K 2300/00; A61K 2039/505; A61K 45/06; A61K 39/00; A61K 47/48561; A61K 47/48569; A61K 39/39; A61K 47/48415; A61K 2039/53; A61K 35/28; A61K 39/0011; A61K 39/21; A61K 47/48584; A61K 2039/5256; A61K 2039/05
See application file for complete search history.

(56) References Cited

U.S. PATENT DOCUMENTS

2006/0004189 A1*  1/2006 Gandy ................. C07K 14/475
530/399

FOREIGN PATENT DOCUMENTS

WO    WO 2005065269 A2 *    7/2005

OTHER PUBLICATIONS

Garin, Eduardo et al. Cytokine from Peripheral Blood Mononuclear Cells (PBMC) from Idiopathic Minimal Lesion Nephrotic Syndrome (ILMNS) Patients in Relapse Induces Albuminuria and Fusion of Foot Processes in Vivo in the Rat. Pediatric Research. 1999. pp. 1-2.*
Lichtenauer, Michael et al. Secretome of apoptotic peripheral blood cells (APOSEC) confers cytoprotection to cardiomyocytes and inhibits tissue remodellingafter acute myocardial infarction: a preclinical study. Basic Res Cardiol 106(6). 2011. pp. 1283-1297.*
Dictionary.com. "Apheresis". Definition retrieved from the Dictionary. com website on Apr. 8, 2014. <http://dictionary.reference.com/browse/apheresis?s=t >.*
Sanguine Biosciences, Andrea. Types of Immune Cells Present in Human PBMC. PBMC Basics. Sanguine Biosciences. (2012). Retrieved from the Sanguine Bioscience website: < http://technical.sanguinebio.com/types-of-immune-cells-present-in-human-pbmc/# >.*
Korf-Klingebiel, Mortimer et al. Bone marrow cells are a rich source of growth factors and cytokines: implications for cell therapy trials after myocardial infarction. European Heart Journal (2008) 29, 2851-2858.*
Supplemental material Table S1. Differentially expressed secreted factors as detected by ProteinChip array. pp. 1-11.*
Klingebiel (Bone marrow cells are a rich source of growth factors and cytokines: implications for cell therapy trials after myocardial infarction, 2008).*
Yoshino (Differential Induction from X-irradiated Human Peripheral Blood Monocytes to Dendritic Cells, 2008).*
Wellman, S. et al., "Specific Reverse Transcription—PCR Quantification of Vascular Endothelial Growth Factor (VEGF) Splice Variants by LightCycler Technology", Clinical Chemistry 47:4 (2001) pp. 654-660.
Kadl, A., et al., "Analysis of inflammatory gene induction by oxidized phospholipids in vivo by quantitative real-time RT-PCR in comparision with effects of LPS", Vascular Pharmacoloy 38 (2002) pp. 219-227.
Trescher, K., et al., "Inflammation and postinfarct remodeling: Overexpression of IkB prevents ventricular dilation via increasing TIMP levels", Cardiovascular Research 69 (2006) pp. 746-754.
Kerjaschki, D., et al., "Lymphatic Neoangiogenesis in Human Kidney Transplants is Associated with Immunologically Active Lymphocytic Infiltrates", J. Am. Soc. Nephrol. 15 (2004) pp. 603-612.
Holzinger, C., et al., "Treatment of Non-healing Skin Ulcers with Autologous Activated Mononuclear Cells", Eur J. Vasc. Surg. 8 (1994) pp. 351-356.
Hojo Yukihiro et al., "Expression of vascular endothelial growth factor in patients with acute myocardial infarction" Journal of the American College of Cardiology, vol. 35, Nr. 4, pp. 968-973, Mar. 15, 2000.

(Continued)

*Primary Examiner* — Nghi V Nguyen
(74) *Attorney, Agent, or Firm* — Workman Nydegger

(57) ABSTRACT

The present invention relates to a pharmaceutical preparation for treating an inflammatory condition, preferably a condition associated with ischemia comprising: a) a physiological solution comprising peripheral blood mononuclear cells (PBM-Cs) or a subset thereof, or b) a supernatant of the solution a), wherein the solution a) is obtainable by cultivating PBMCs or a subset thereof in a physiological solution free of PBMC-proliferating and PBMC-activating substances for at least 1 h.

20 Claims, 33 Drawing Sheets
Specification includes a Sequence Listing.

(56) References Cited

OTHER PUBLICATIONS

Tatsumi Tetsuya et al., "Intracoronary transplantation of non-expanded peripheral blood-derived mononuclear cells promotes improvement of cardiac function in patients with acute myocardial infarction", Circulation Journal, vol. 71, Nr. 8, pp. 1199-1207, Aug. 2007.

Tuchinda Chanisada et al., "Comparison of broadband UVB, narrowband UVB, broadband UVA and UVA1 on activation of apoptotic pathways in human peripheral blood mononuclear cells", Photodermatology Photoimmunology & Photomedicine, vol. 23, No. 1, pp. 2-9, Feb. 2007.

Doyle Brendan et al., "Progenitor cell therapy in a porcine acute myocardial infarction model induces cardiac hypertrophy, mediated by paracrine secretion of cardiotrophic factors including TGFbeta1", Stem Cells and Development, vol. 17, No. 5, pp. 941-951, Oct. 1, 2008.

Golpon Heiko, A., et al., "Life after corpse engulfment: phagocytosis of apoptotic cells leads to VEGF secretion and cell growth", FASEB Journal, vol. 18, No. 12, pp. 2, 8, 949, Sep. 2004.

Ankersmit, H. J., et al., "Irradiated cultured apoptotic peripheral blood mononuclear cells regenerate infarcted myocardium", European Journal of Clinical Investigation, vol. 39, Nr. 6, pp. 445-456, Jun. 2009.

EP 08450199 Search Report dated Dec. 11, 2009.

PCT/EP2009/067536 Written Opinion of the International Search Report.

PCT/EP2009/067536 International Preliminary Report on Patentability.

Lichtenauer, M., et al., "Secretome of apoptotic peripheral blood cells (APOSEC) confers cytoprotection to cardiomyocytes and inhibits tissue remodelling after acute myocardial infarction: a preclinical study", Basic Res. Cardiol. (2011) 106: 1283-1297.

Ghezzi et al., "Hypoxia increases production of interleukin-1 and tumor necrosis factor by human mononuclear cells," Cytokine. 3(3):189-94 (1991).

Mühl et al., "Expression and release of chemokines associated with apoptotic cell death in human promonocytic U937 cells and peripheral blood mononuclear cells", Eur J Immunol, 29(10):3225-35 (1999).

Koch-Piaz et al., "Functional genomics of UV radiation responses in human cells," Mutation Research 549, 65-78 (2004).

Kesic et al., "Exposure to Ozone Modulates Human Airway Protease/Antiprotease Balance Contributing to Increased Influenza A Infection," PLoS One, 2012;7(4):e35108. doi: 10.1371/journal.pone.0035108. Epub Apr. 9, 2012. (Abstract).

Rattan et al., "Heat Stress and Hormetin-Induced Hormesis in Human Cells: Effects on Aging, Wound Healing, Angiogenesis, and Differentiation," Dose Response, 2009; 7(1): 90-103.

Hjelmeland et al., "Acidic stress promotes a glioma stem cell phenotype" Cell Death Differ, May 2011; 18(5): 829-840.

\* cited by examiner d e

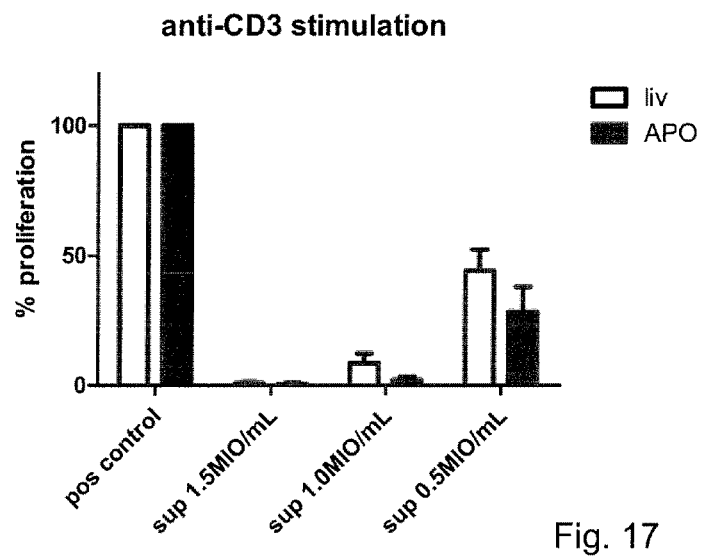
Fig. 17
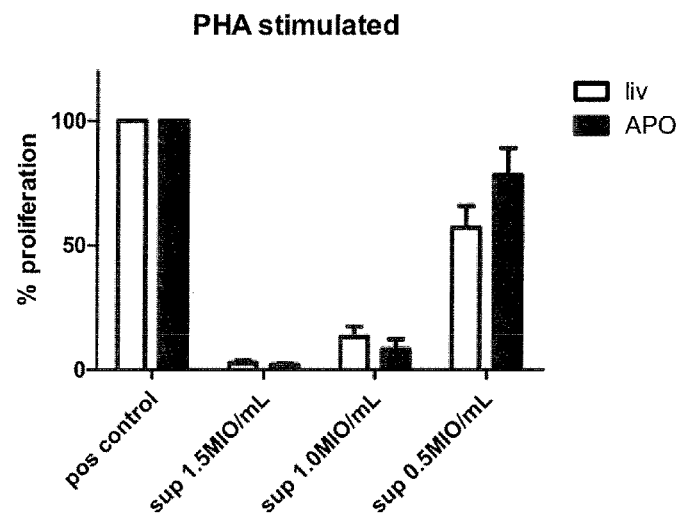

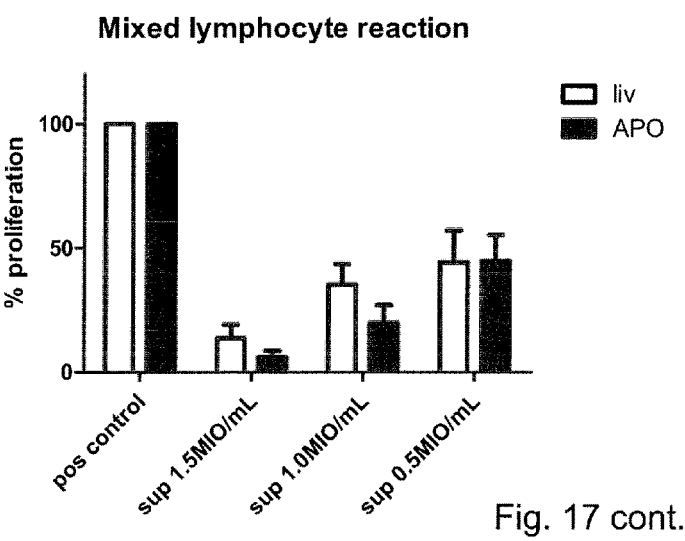
Fig. 17 cont.
Fig. 18
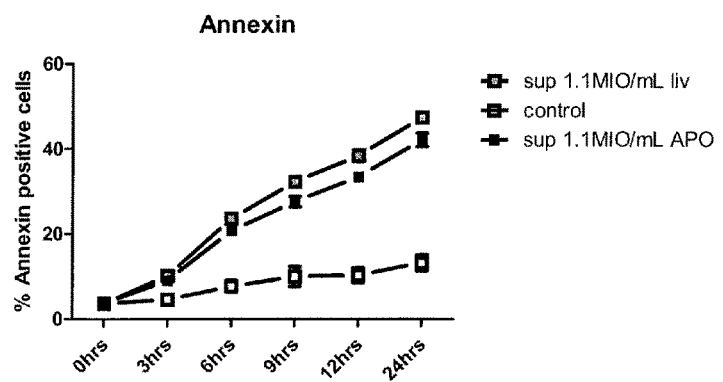

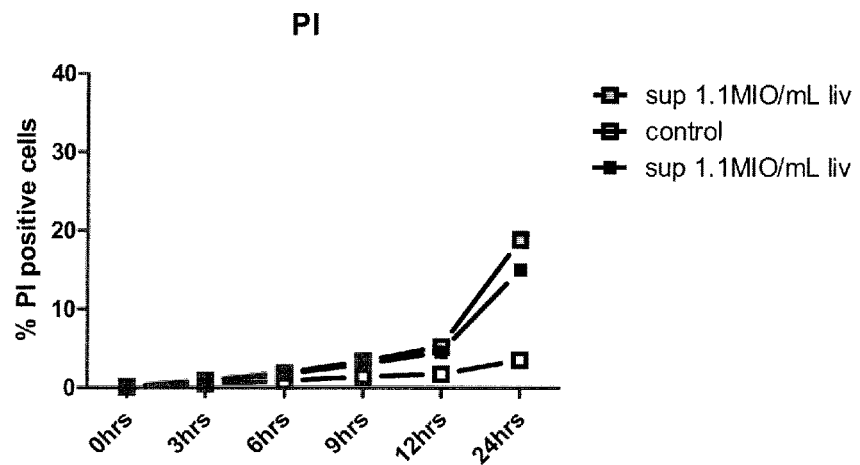
Fig. 18 cont.
Fig. 19
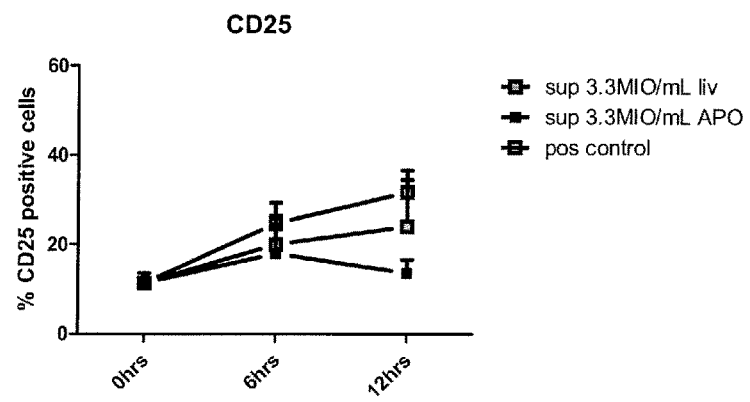

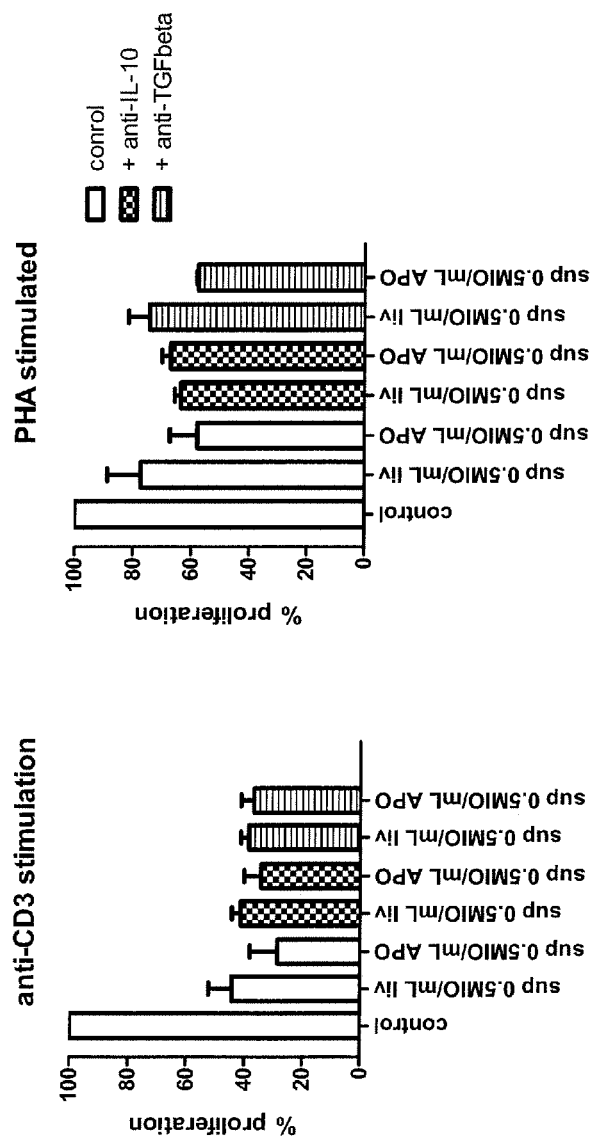

PHARMACEUTICAL PREPARATION

This application is a national phase application of PCT/EP2009/067536, filed Dec. 18, 2009, which claims priority to European Patent Application No. 08450199.8 filed Dec. 18, 2008, the disclosures of which are incorporated herein by reference in their entirety.

BACKGROUND OF THE INVENTION

Field of the Invention

Sequence Listing

The instant application contains a Sequence Listing which has been submitted electronically in ASCII format and is hereby incorporated by reference in its entirety. Said ASCII copy, created on Mar. 5, 2014, is named 34128-00003_SL.txt and is 2,103 bytes in size.

Description of Related Art

The present invention relates to a pharmaceutical preparation for treating internal inflammatory conditions, preferably internal conditions associated with ischemia.

Hypoxia, a state of reduced oxygen, can occur when the lungs are compromised or blood flow is reduced. Ischemia, reduction in blood flow, can be caused by the obstruction of an artery or vein by a blood clot (thrombus) or by any foreign circulating matter (embolus) or by a vascular disorder such as atherosclerosis. Reduction in blood flow can have a sudden onset and short duration (acute ischemia) or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain and heart, producing disorders such as intestinal infarction, pulmonary infarction, ischemic stroke and myocardial infarction.

Pathologic changes in ischemic disorders depend on the duration and severity of ischemia, and on the length of patient survival. Necrosis can be seen within the infarct in the first 24 h and an acute inflammatory response develops in the viable tissue adjacent to the infarct with leukocytes migrating into the area of dead tissue. Over succeeding days, there is a gradual breakdown and removal of cells within the infarct by phagocytosis and replacement with a collagenous or glial scar.

Hypoperfusion or infarction in one organ often affects other organs. For example, ischemia of the lung, caused by, for example, a pulmonary embolism, not only affects the lung, but also puts the heart and other organs, such as the brain, under hypoxic stress. Myocardial infarction, which often involves coronary artery blockage due to thrombosis, arterial wall vasospasms, or viral infection of the heart, can lead to congestive heart failure and systemic hypotension. Secondary complications such as global ischemic encephalopathy can develop if the cardiac arrest is prolonged with continued hypoperfusion. Cerebral ischemia, most commonly caused by vascular occlusion due to atherosclerosis, can range in severity from transient ischemic attacks (TIAs) to cerebral infarction or stroke. While the symptoms of TIAs are temporary and reversible, TIAs tend to recur and are often followed by a stroke.

Occlusive arterial disease includes coronary artery disease, which can lead to myocardial infarction, and peripheral arterial disease, which can affect the abdominal aorta, its major branches, and arteries of the legs. Peripheral arterial disease includes Buerger's disease, Raynaud's disease, and acrocyanosis. Although peripheral arterial disease is commonly caused by atherosclerosis, other major causes include, e.g., diabetes, etc. Complications associated with peripheral arterial disease include severe leg cramps, angina, abnormal heart rhythms, heart failure, heart attack, stroke and kidney failure.

Ischemic and hypoxic disorders are a major cause of morbidity and mortality. Cardiovascular diseases are responsible for 30% of deaths worldwide. Among the various cardiovascular diseases, ischemic heart disease and cerebrovascular diseases cause approximately 17% of deaths.

Currently, treatment of ischemic and hypoxic disorders is focused on relief of symptoms and treatment of causative disorders. For example, treatments for myocardial infarction include nitroglycerin and analgesics to control pain and relieve the workload of the heart. Other medications, including digoxin, diuretics, amrinone, beta-blockers, lipid-lowering agents and angiotensin-converting enzyme inhibitors, are used to stabilize the condition, but none of these therapies directly address the tissue damage produced by the ischemia and hypoxia.

Due to deficiencies in current treatments, there remains a need for methods that are effective in treating conditions involving hypoxia. There is also a need for methods that are effective in the prevention of tissue damage caused by ischemia that occurs due to, e.g., atherosclerosis, diabetes and pulmonary disorders.

Conditions associated with ischemia and hypoxia are usually accompanied by inflammation. Therefore means and methods are needed which also reduce inflammation.

BRIEF SUMMARY OF THE INVENTION

It is an object of the present invention to provide means which allow the efficient treatment of internal inflammatory conditions, preferably conditions associated with ischemia.

The present invention relates to a pharmaceutical preparation for treating an internal inflammatory condition, preferably an internal condition associated with ischemia, comprising a) a physiological solution comprising peripheral blood mononuclear cells (PBMCs) or a subset thereof, or b) a supernatant of the solution a), wherein the solution a) is obtainable by cultivating PBMCs or a subset thereof in a physiological solution free of PBMC-proliferating and PBMC-activating substances for at least 1 h.

It turned out that the administration of a pharmaceutical preparation as defined above to a patient suffering from an internal inflammatory condition, preferably an internal condition associated with ischemia, results in an alleviation of the respective symptoms and in a healing process.

BRIEF DESCRIPTION OF THE DRAWINGS

FIG. 2 (b) is a graph of co-incubation of LPS stimulated PBMC or monocytes with irradiated apoptotic autologous PBMC.

FIG. 2 (c) is a graph of IL-6 secretion profile of LPS stimulated PBMC and monocytes in the presence of IA-PBMC.

FIG. 2(d) is a graph of autologous IA-PBMC in a mixed lymphocyte reaction with LPS stimulation.

FIG. 2 (e) is a graph of RT-PCR RNA expression of VEGF, IL-8/CXCL8 and MMP transcripts.

FIG. 2 (f) is a graph of ELISA VEGF, IL-8/CXCL8 and MMP9.

FIG. 2 (g) is a graph of human fibroblasts incubated in supernatants.

FIGS. 3 j, k, l show higher levels of S100β+ cells were found in rats receiving medium alone compared to the application of viable PBMC or IA-PBMC.

FIGS. 4 d, e, f show expression patterns for VEGF receptor KDR/FLK1

FIGS. 4 g, h, i show detected CD34 in all three groups (d, e, f).

FIGS. 4. j, k, l show immunohistogical analysis for the marker c-kit.

FIG. 5(d) is a statistical analysis of data obtained from planimetric analysis of specimen collected 6 weeks after LAD-ligation.

FIG. 5e, f, and g show assessment of cardiac function parameters shortening fraction, ejection fraction and end-systolic diameter.

FIG. 17 shows the proliferation of PBMC upon stimulation with anti-CD3, PHA and mixed lymphocytes.

FIG. 18 shows the level of Annexin V and PI positivity of the supernatant of CD4+ cells inocubated with PBMC supernatants.

FIG. 20 shows that the demonetizing of IL-10 and TGF-β did not increase the proliferation rates of CD4+ cells.

DETAILED DESCRIPTION OF THE INVENTION

Figure 1:
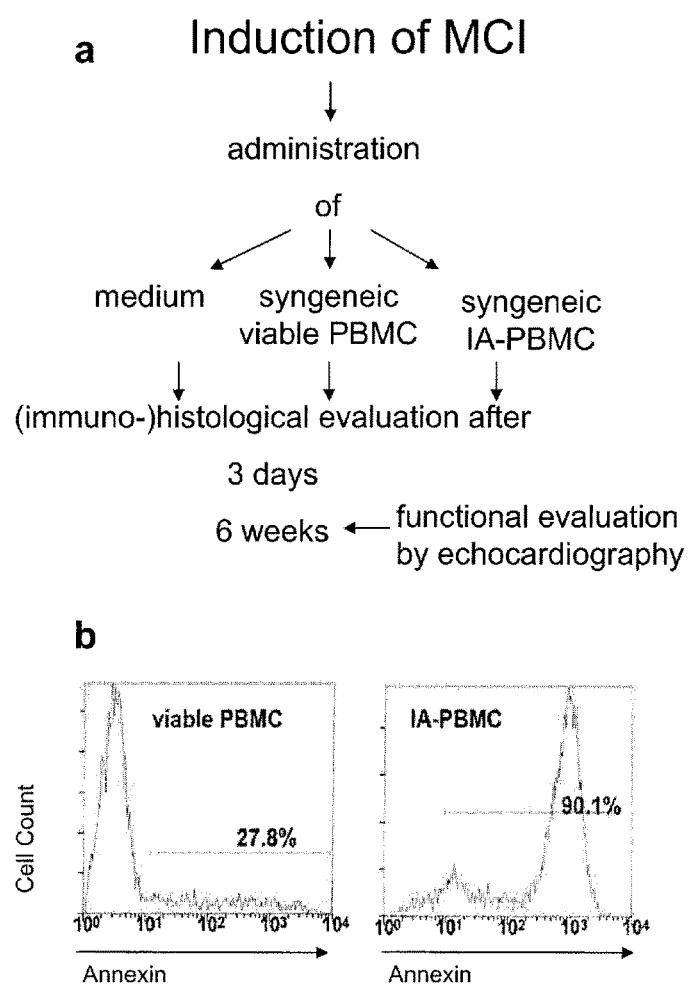
FIG. 1a is a flowchart of Induction of MCI.
FIG. 1b is a graph of the percentage of irradiated and non-irradiated rat PBMC positively stained for Annexin after a culture period of 18 h.

The pharmaceutical preparation of the present invention comprises cultivated PBMCs or a subset thereof and/or the supernatant in which the PBMCs have been cultivated. In the course of the cultivation of PBMCs these cells express and secrete substances like cytokines which differ from those expressed and secreted in activated PBMCs. This means that the secretome of PBMCs of the present invention is different from the secretome of activated PBMCs. The cells of the present invention undergo a non-cell-surface moiety triggered secretome production. Therefore it is surprising that PBMCs which have not been contacted with PBMC activating substances like PHA or LPS can be employed to treat internal inflammatory conditions, in particular ischemic conditions, which shows that the secretome of these cells comprises substances supporting the treatment of such or similar conditions.

The PBMCs according to the present invention are obtainable by cultivating them in a physiological solution which does not comprise PBMC-proliferating and PBMC-activating substances. However, the PBMCs are incubated in the physiological solution for at least 1 h. This minimum time of cultivation is required to let the PBMCs secrete cytokines and other beneficial substances.

PBMCs part of the preparation according to the present invention can be obtained from whole blood using methods known in the art such as Ficoll gradient, hypotonic lysis etc. These methods are well known in the art.

PBMCs of the pharmaceutical preparation may be obtained from a pool of donors or from the same individual to which the preparation will be administered.

The PBMCs or the subsets thereof are present in the preparation according to the present invention in their viable form.

The physiological solution from which the supernatant is obtained comprises at least 500, preferably at least 1000, more preferably at least $10^5$, even more preferably at least $10^6$, cells per ml solution or per dosage unit.

The preparation of the present invention may comprise at least 500, preferably at least 1000, more preferably at least $10^5$, even more preferably at least $10^6$, PBMCs per ml or per dosage unit.

"Physiological solution", as used herein, refers to a liquid solution in which PBMCs are cultivated prior their use in the pharmaceutical preparation according to the present invention.

"Physiological solution" refers also to a solution which does not lead to the death of PBMCs within an hour, preferably within 30 min. If the number of viable PBMCs is decreasing in a solution by 75%, more preferably by 90% within one hour, preferably within 30 min, the solution is not considered to be a "physiological solution" as defined herein. The "physiological solution" does not lead to a spontaneous lysis of PBMCs when contacted with said solution.

In this context the step of "cultivating" or "culturing" comprises or consists of the step of "incubating", a step in which the cells are contacted with a solution for a defined time (at least 1 h, preferably at least 4 h, more preferably at least 8 h, even more preferably at least 12 h) under conditions which are regularly used for cultivating PBMCs.

The term "condition associated with ischemia" in the context of the present invention can be used interchangeable with the term "ischemic conditions" and denotes any condition, disease or disorder in which regions of the human or animal body are deprived of adequate oxygen supply resultant damage or dysfunction of tissue. A pathological condition may be characterized by reduction or abolition of blood supply within an organ or part of an organ, which may be caused by the constriction or obstruction of a blood vessel. Such conditions are collectively referred to herein by the term "ischemia" or "ischemia related conditions" or "condition related to ischemia". In heart disease, for instance, ischemia is often used to describe the heart muscle that is not getting the proper amount of oxygen-rich blood because of narrowed or blocked coronary arteries. The symptoms of ischemia depend on the organ that is "ischemic". With the heart, ischemia often results in angina pectoris. In the brain, ischemia can result in a stroke. Ischemia conditions are accompanied by inflammation.

Non-limiting examples for pathological conditions which relate to inflammation, in particular to ischemia, include wounds, myocardial ischemia, limb ischemia, tissue ischemia, ischemia-reperfusion injury, angina pectoris, coronary artery disease, peripheral vascular disease, peripheral arterial disease, stroke, ischemic stroke, chronic wounds, diabetic wounds, myocardial infarct, congestive heart failure, pulmonary infarction, skin ulcer, etc.

Notwithstanding the above, a pathological condition in the context of the invention may be characterized by damage or dysfunction of endothelial cells, i.e. wound. Non-limiting examples of wounds which may be treated by the use of the preparation according to the present invention are chronic wounds, diabetic wounds, ulcer, burns, inflammatory skin disease and bowel disease.

The terms "internal condition", "internal inflammatory condition" and "internal conditions associated with ischemia" relate to conditions and diseases which occur inside the body of an individual that are caused by acute or latent hypoxia and inflammation in mammal end organs necessary for optimal functioning (e.g. bone, heart, liver, kidney, cerebrum, skin integrety).

"Physiological solution", as used herein, refers to a solution exhibiting an osmotic pressure which does not lead to the destruction of the PBMCs or subsets thereof and can be directly administered to an individual.

The term "free of PBMC-proliferating and PBMC-activating substances" refers to the physiological solution which does not comprise substances which activate PBMCs and induce the proliferation of PBMCs or subsets thereof. These substances include PHA, LPS etc.

According to a preferred embodiment of the present invention the inflammatory condition is selected from the group of mammal diseases that are related to hypoxia and inflammation of functional end organs.

According to a particularly preferred embodiment of the present invention the internal inflammatory condition, preferably the internal condition associated with ischemia, is selected from the group consisting of myocardial ischemia, limb ischemia, tissue ischemia, ischemia-reperfusion injury, angina pectoris, coronary artery disease, peripheral vascular disease, peripheral arterial disease, stroke, ischemic stroke, myocardial infarct, congestive heart failure, trauma, bowel disease, mesenterial infarction, pulmonary infarction, bone fracture, tissue regeneration after dental grafting, auto-immune diseases, rheumatic diseases, transplantation allograft and rejection of allograft.

The subset of peripheral blood mononuclear cells (PBMCs) is preferably T cells, B cells or NK cells. Of course it is also possible to use combinations of these cells: T cells and B cells; T cells and NK cells; B cells and NK cells; T cells, B cells and NK cells. Methods for providing and isolating said cells are known.

It surprisingly turned out that the PBMCs of the present invention can be cultivated in any kind of solution provided that said solution does not comprise substances which are not pharmaceutically acceptable, lead to an immediate death of the PBMCs, activate PBMCs and stimulate the proliferation of PBMCs (as defined above). Therefore the solution to be used at least exhibits osmotic properties which do not lead to lysis of the PBMCs. The physiological solution is preferably a physiological salt solution, preferably a physiological NaCl solution, whole blood, a blood fraction, preferably serum, or a cell culture medium.

The cell culture medium is preferably selected from the group consisting of RPMI, DMEM, X-vivo and Ultraculture.

According to a particularly preferred embodiment of the present invention the cells of the present invention are cultivated under stress inducing conditions.

The term "under stress inducing conditions", as used herein, refers to cultivation conditions leading to stressed cells. Conditions causing stress to cells include among others heat, chemicals, radiation, hypoxia, osmotic pressure (i.e. non-physiological osmotic conditions) etc.

Additional stress to the cells of the present invention leads to a further increase of the expression and secretion of substances beneficial for treating internal inflammatory conditions, preferably internal conditions associated with ischemia.

According to a preferred embodiment of the present invention the stress inducing conditions include hypoxia, ozone, heat (e.g. more than 2° C., preferably more than 5° C., more preferably more than 10° C., higher than the optimal cultivation temperature of PBMCs, i.e. 37° C.), radiation (e.g. UV radiation, gamma radiation), chemicals, osmotic pressure (i.e. osmotic conditions which are elevated at least 10% in comparison to osmotic conditions regularly occurring in a body fluid, in particular in blood), pH shift or combinations thereof.

If radiation is used to stress the PBMCs of the present invention the cells are preferably irradiated with at least 10 Gy, preferably at least 20 Gy, more preferably at least 40 Gy, whereby as source Cs-137 Caesium is preferably used.

According to a preferred embodiment of the present invention the non-activated PBMCs or a subset thereof are cultivated in a medium for at least 4 h, preferably for at least 6 h, more preferably for at least 12 h.

The pharmaceutical preparation according to the present invention can be administered in various ways depending on the condition to be treated. Therefore said preparation is preferably adapted for subcutaneous administration, intramuscular administration, intra-organ administration (e.g. intramyocardial administration) and intravenous administration.

A pharmaceutical preparation according to the present invention may comprise pharmaceutically acceptable excipients such as diluents, stabilizers, carriers etc. Depending on the administration route the preparation according to the present invention is provided in a respective dosage form: injection solution, etc. Methods for preparing the same are well known to the skilled artisan.

In order to increase the shelf-life of the preparation according to the present invention the solution a) or the supernatant b) is lyophilised. Methods for lyophilising such preparations are well known to the person skilled in the art.

Prior its use the lyophilised preparation can be contacted with water or an aqueous solution comprising buffers, stabilizers, salts etc.

Another aspect of the present invention relates to the use of a preparation as defined above for the manufacture of a medicament for treating an internal inflammatory condition, preferably an internal condition associated with ischemia.

Yet another aspect of the present invention relates to a method for preparing a pharmaceutical preparation as disclosed herein comprising the steps of a) providing peripheral blood mononuclear cells (PBMCs) or a subset thereof, b) culturing the cells of step a) in a physiological solution free of PBMC-proliferating and PBMC-activating substances for at least 1 h, c) isolating the cells of step b) and/or the supernatant thereof, and d) preparing the pharmaceutical preparation using the cells and/or the supernatant of step c).

The preparation according to the present invention can be obtained by incubating or culturing PBMCs in a physiological solution for at least 1 h, preferably at least 4 h, more preferably at least 8 h, even more preferably at least 12 h. In the course of this step the PBMCs begin to synthesize and to secrete substances which are useful in the treatment of internal inflammatory conditions. Prior, after and in the course of the culturing step the cells are not activated by adding PBMC activating substances like PHA or LPS. After the cultivation step the cells and/or the supernatant of the culture is isolated to be further used in the preparation of the final pharmaceutical preparation. As discussed above the pharmaceutical preparation may comprise cultivated PBMCs, the supernatant of the culture in which said cells had been incubated or both the cultivated PBMCs as well as the culture medium.

According to a preferred embodiment of the present invention the cells are subjected to stress inducing conditions before or in the course of step b), wherein said stress inducing conditions include hypoxia, ozone, heat, radiation, chemicals, osmotic pressure (e.g. induced by the addition of salt, in particular NaCl, in order to give an osmotic pressure higher than in blood), pH shift (i.e. pH change by adding acids or hydroxides to give a pH value of 6.5 to 7.2 or 7.5 to 8.0) or combinations thereof.

According to a preferred embodiment of the present invention the cells are irradiated before or in the course of step b) with at least 10 Gy, preferably at least 20 Gy, more preferably at least 40 Gy, with ozone, with elevated temperature or with UV radiation.

Another aspect of the present invention relates to a preparation obtainable by a method as described above.

Another aspect of the present invention relates to a method for treating internal inflammatory conditions, preferably internal conditions associated with ischemia, by administering to an individual in need thereof an appropriate amount of the pharmaceutical preparation according to the present invention. Depending on the condition to be treated the preparation of the present invention is administered intramuscularly, intravenously, intra-organly (e.g. intramyocardially) or subcutaneously.

In a preferred embodiment of the present invention the pharmaceutical preparation comprises at least 500, preferably at least 1000, more preferably at least $10^5$, even more preferably at least $10^6$ PBMCs per ml obtainable by a method as outlined above. Correspondingly at least 500, preferably at least 1000, more preferably at least $10^5$, even more preferably at least $10^6$, PBMCs are administered to an individual to be treated.

The present invention is further illustrated by the following figures and examples, however, without being restricted thereto.

FIG. 1 shows: (a) the study protocol and the time points of evaluation of cardiac function by echocardiography, histology and immunohistology; (b) the percentage of irradiated and non-irradiated rat PBMC positively stained for Annexin after a culture period of 18 h.

Figure 2:
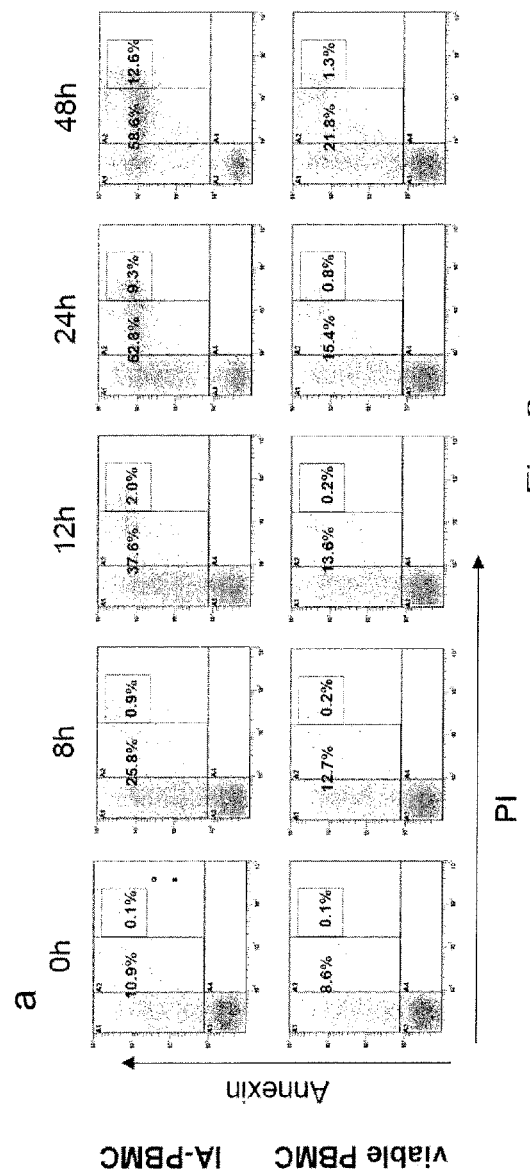
FIG. 2 (a): FACS graph of irradiation and apoptosis.
Figure 2:
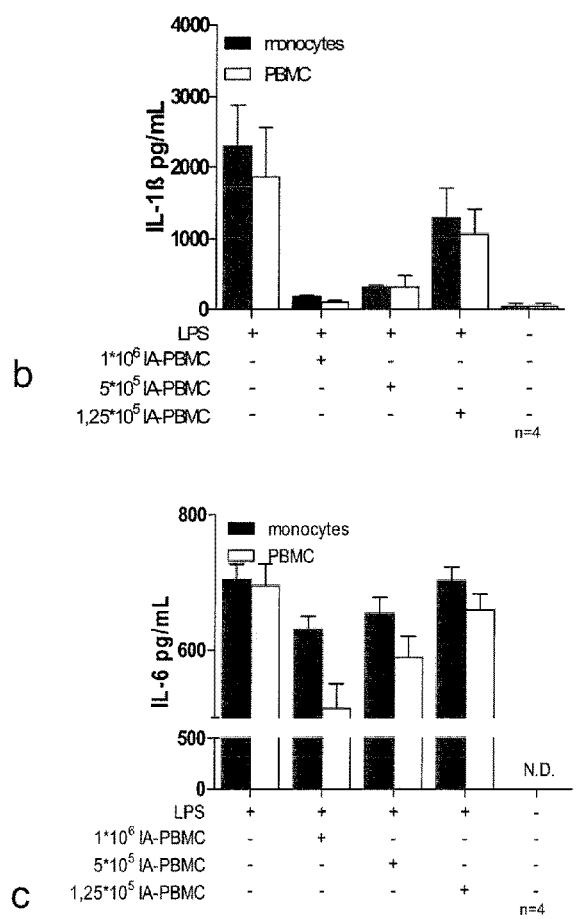
Figure 2:
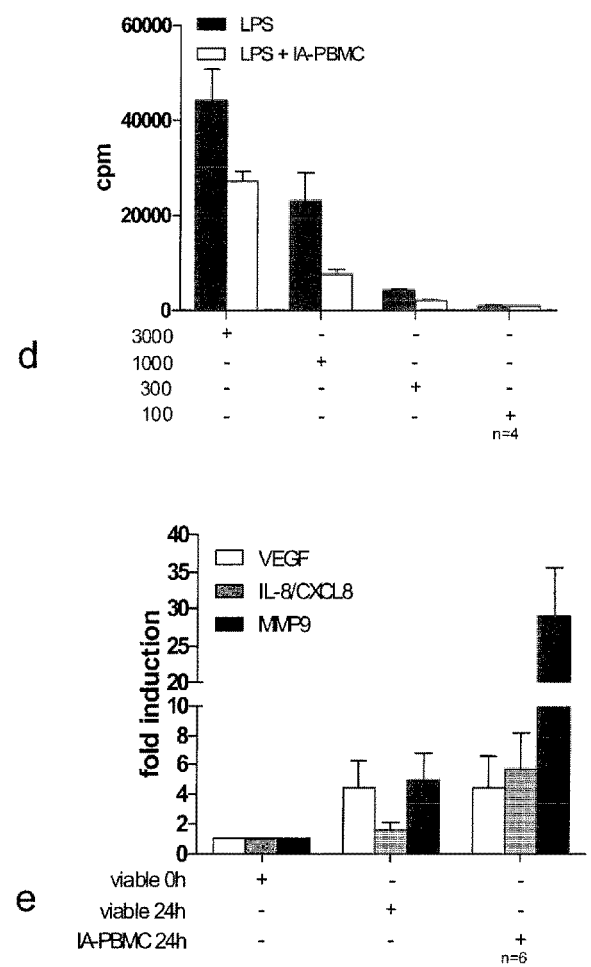
Figure 2:
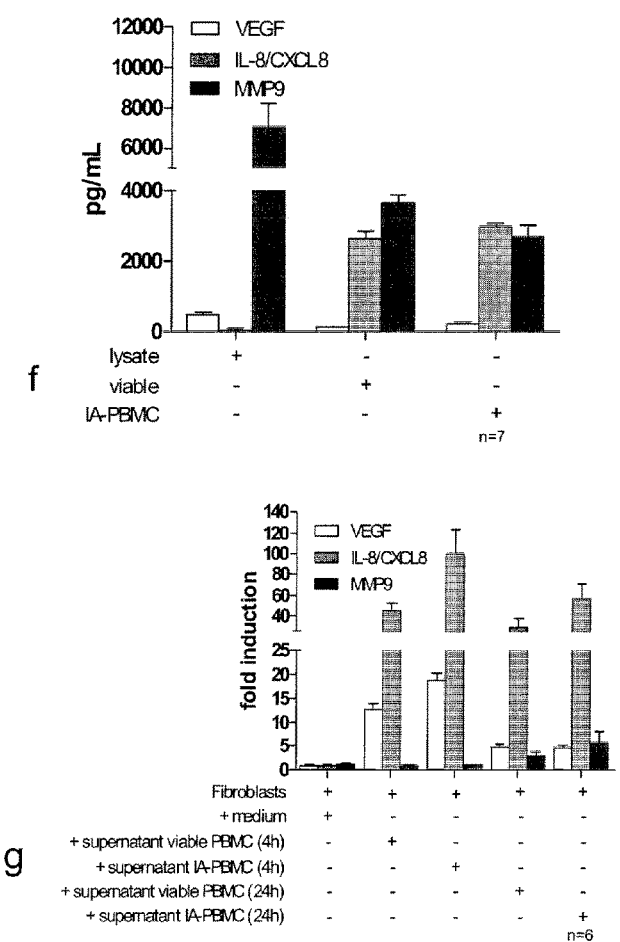

FIG. 2 (a): FACS analysis shows that irradiation leads to induction of apoptosis in human PBMC with a time dependent increase of Annexin expression over 48 h. (b) Co-incubation of LPS stimulated PBMC or monocytes with irradiated apoptotic autologous PBMC demonstrates a reduced secretion of the proinflammatory cytokine IL-1β in a dose dependent manner. (c) To a lesser extent this finding also correlates with the IL-6 secretion profile of LPS stimulated PBMC and monocytes in the presence of IA-PBMC. (d) Addition of autologous IA-PBMC in a mixed lymphocyte reaction with LPS stimulation decreases T-cell proliferation as measured by counts per minute (cpm). (e) RT-PCR RNA expression analysis of VEGF, IL-8/CXCL8 and MMP transcripts shows an upregulation of IL-8/CXCL8 and especially MMP9 in irradiated PBMC after a culture period of 24 h. (f) ELISA analysis of VEGF, IL-8/CXCL8 and MMP9 demonstrates that MMP9 is predominantly found in cell lysates whereas differences in VEGF and IL-8/CXCL8 protein secretion remain approximately at the same level in both viable cells and IA-PBMC. (g) Human fibroblasts incubated in supernatants obtained from cell cultures of viable or IA-PBMC exhibit a strong upregulation of VEGF, IL-8/CXCL8 and MMP9 transcripts in RT-PCR analysis, peak values were found in fibroblasts incubated in IA-PBMC supernatants.

Figure 3:
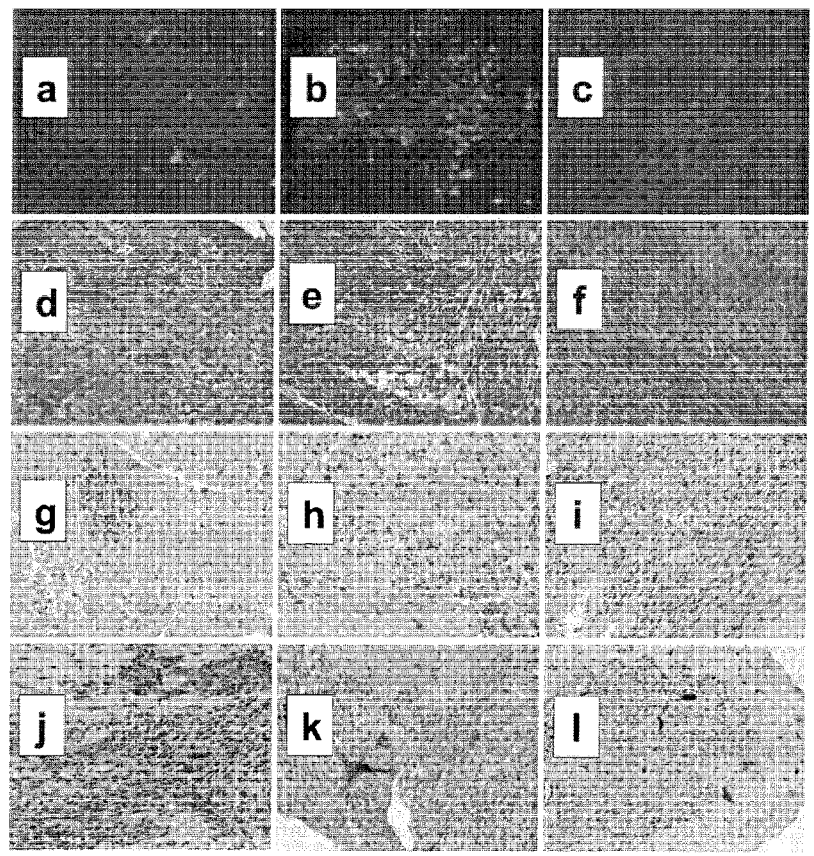
FIGS. 3 a, b, c show CFSE labeled syngeneic PBMC administered via the tail vein in rats after artificial myocardial infarction were predominantly found in the spleen (b), to a lesser extent in the liver FIGS. 3 d, e, f show HE stained infarct zones of rats injected with either medium FIGS. 3 g, h, and i show the results from rats treated with viable cells.
Figure 3:
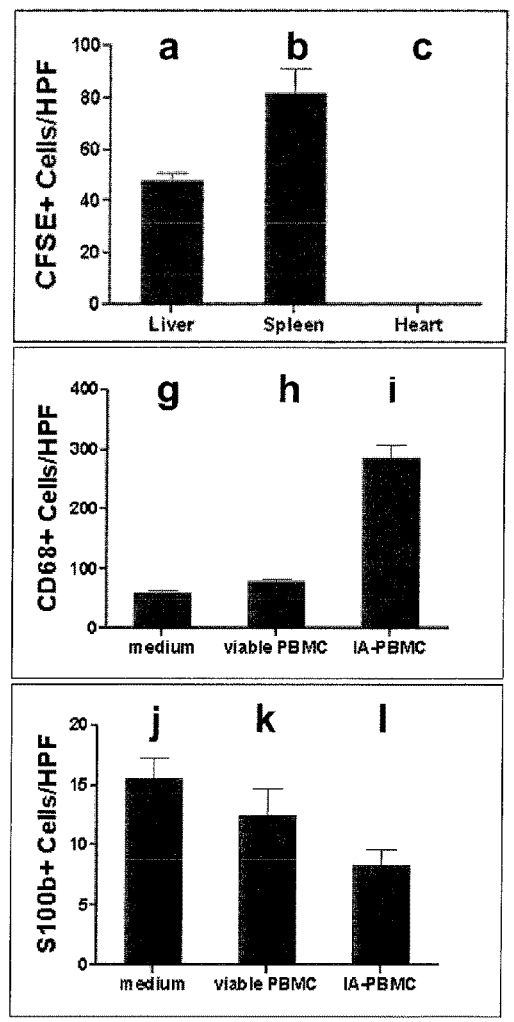

FIG. 3 (a, b, c): CFSE labeled syngeneic PBMC administered via the tail vein in rats after artificial myocardial infarction were predominantly found in the spleen (b), to a lesser extent in the liver (a) and no cells in the infarcted heart (c). (d, e, f): HE stained infarct zones of rats injected with either medium (d) or viable PBMC (e) show a comparable pattern of ischemic myocardium infiltrated by immune cells, tissues obtained from rats receiving IA-PBMC indicate very dense infiltrations. (g, h, i): Rats treated with viable cells (h) reveal sightly more of CD68+ stained cells in the infarcted than in medium treated rats (g), but a 3-fold higher amount of CD68+ was detected in IA-PBMC injected animals. (j, k, l): Higher levels of S100β+ cells were found in rats receiving medium alone compared to the application of viable PBMC or IA-PBMC.

Figure 4:
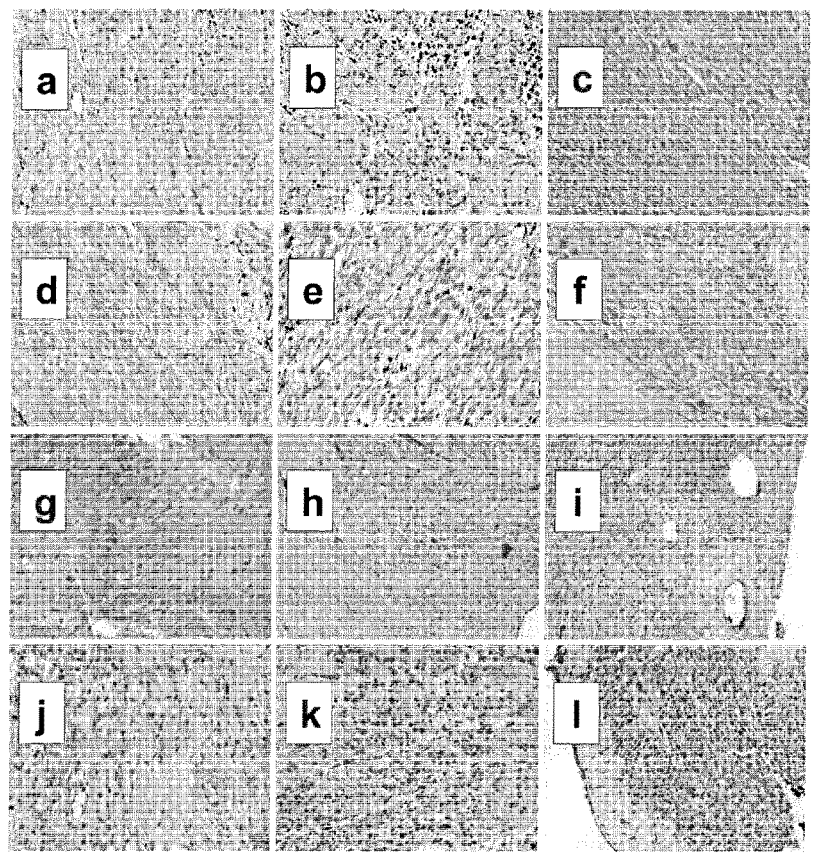
FIGS. 4 a, b, c graphs amounts of cells staining positive for VEGF were detected in infarcted myocardial tissue obtained from animals injected with IA-PCMC (c), in comparison with medium (a) or viable cell treatment (b).
Figure 4:
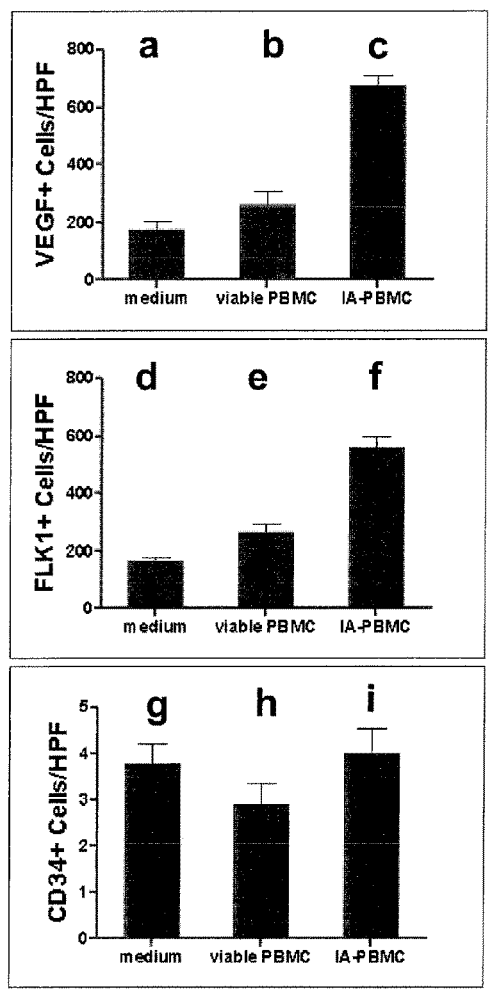
Figure 4:
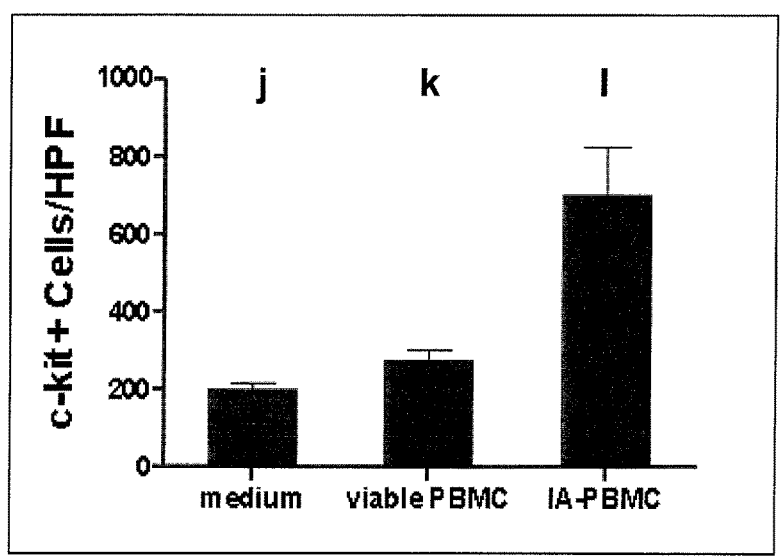

FIG. 4 (a, b, c): Almost 4-fold higher amounts of cells staining positive for VEGF were detected in infarcted myocardial tissue obtained from animals injected with IA-PBMC (c), in comparison with medium (a) or viable cell treatment (b). (d, e, f): A similar expression pattern was found for VEGF receptor KDR/FLK1 with peak values in the IA-PBMC group (f) compared to medium (d) and viable cells (e). (g, h, i): No differences were detected for CD34 in all three groups. (j, k, l) immunchistogical analysis for the marker c-kit in infarcted hearts shows a high quantity of positively stained cells and dense localization in rats injected with IA-PBMC (l) and fewer cells in medium (j) and viable cell receiving animals (k).

Figure 5:
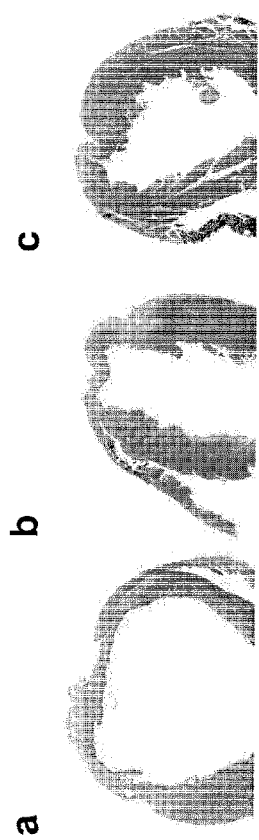
FIG. 5 (a, b, c) show histological analysis of ischemic rat hearts explanted 6 weeks after induction of myocardial infarction.
Figure 5:
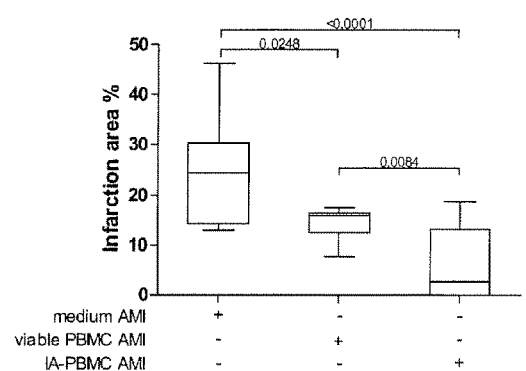
Figure 5:
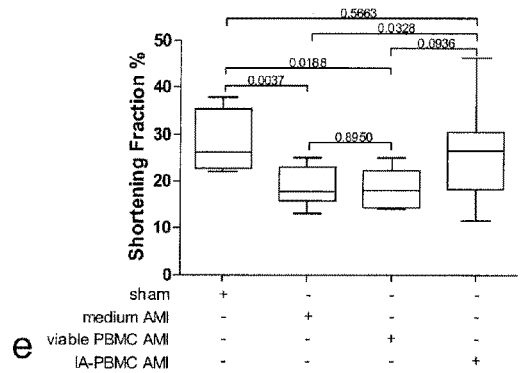
Figure 5:
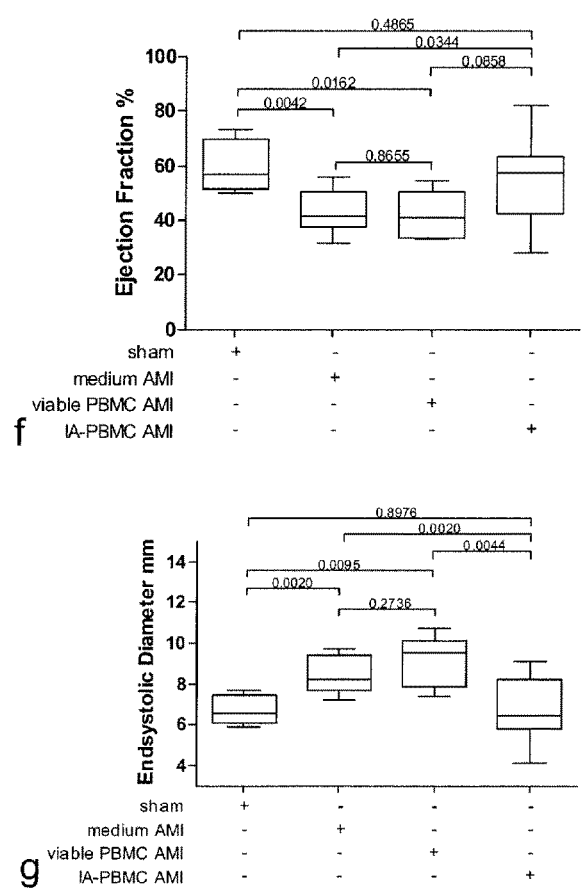

FIG. 5 (a, b, c): Histological analysis of ischemic rat hearts explanted 6 weeks after induction of myocardial infarction (Elastica van Gieson staining), hearts from medium injected animals (a) appear more dilated and show a greater extension of fibrotic tissue, scar extension was reduced in viable cell injected rats (b) with fewer signs of dilatations, the least amount of scar tissue formation was detected in IA-PBMC injected animals (c). (d) statistical analysis of data obtained from planimetric analysis of specimen collected 6 weeks after LAD-ligation shows a mean scar extension of 24.95%±3.6 in medium, of 14.3%±1.3 in viable PBMC and 5.8%±2 in IA-PBMC injected animals (mean+SEM). (e, f, g): Assessment of cardiac function parameters shortening fraction, ejection fraction and end-systolic diameter by echocardiography evidences a better recovery after myocardial infarction in animals injected with IA-PBMC.

Figure 6A:
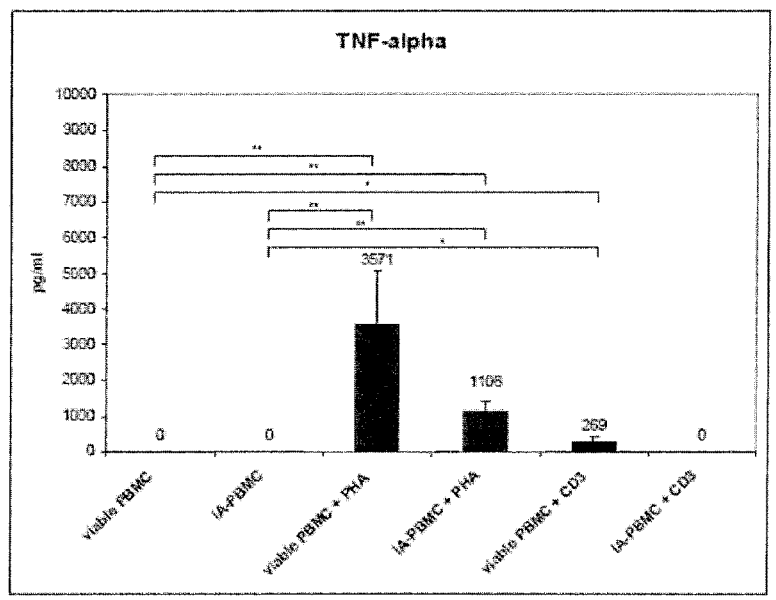
FIG. 6a is a graph of showing that neither unstimulated viable PBMC or IA-PBMC secrete the mainly monocyte derived pro-inflammatory cytokine TNF-α.

FIG. 6a shows that neither unstimulated viable PBMC or IA-PBMC secrete the mainly monocyte derived pro-inflammatory cytokine TNF-α. (Significances are indicated as follows: *p=0.05, **p=0.001; n=8)

Figure 6B:
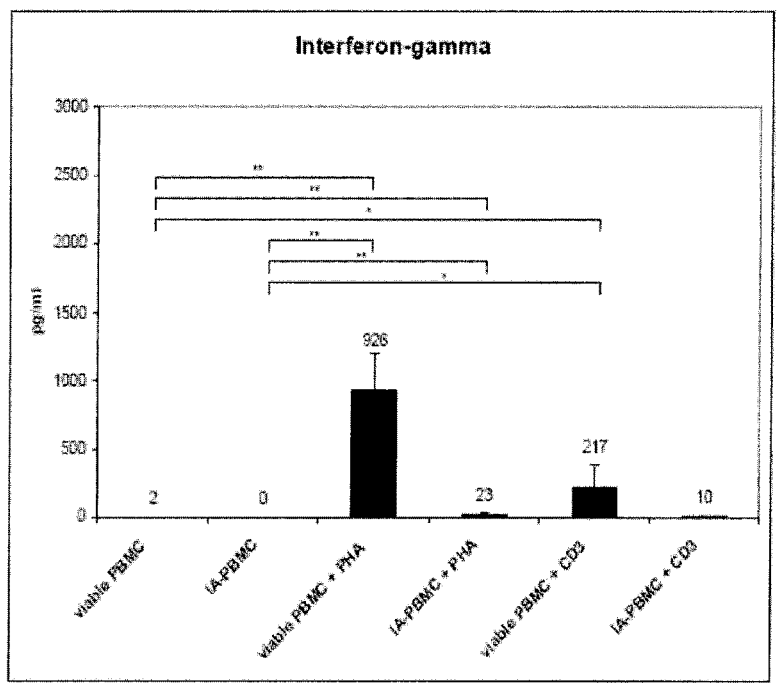
FIG. 6b is a graph showing a strong induction of pro-inflammatory Interferon-y secretion after activation as compared to unstimulated PBMC.

FIG. 6b demonstrates a strong induction of pro-inflammatory Interferon-γ secretion after activation as compared to unstimulated PBMC. (Significances are indicated as follows: *p=0.05, **p=0.001; n=8)

Figure 7A:
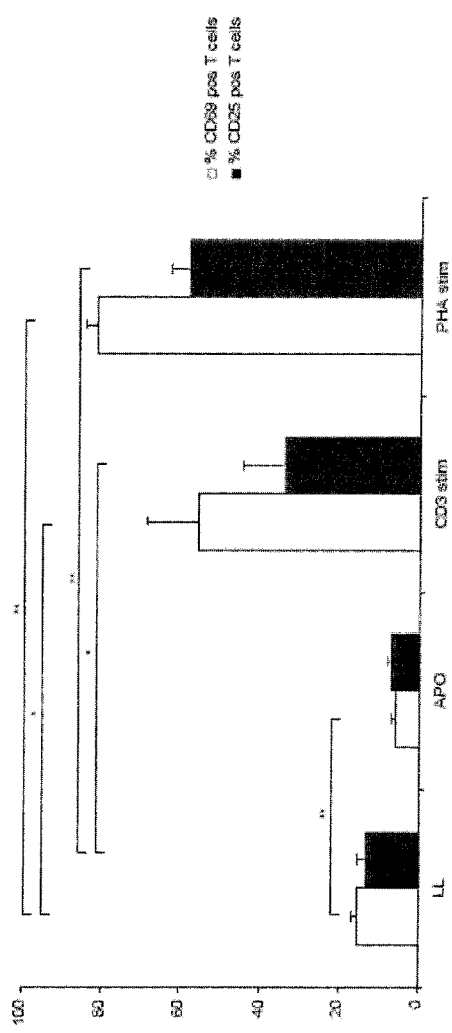
FIG. 7a is a graph of pooled results of flow cytometric analysis.

FIG. 7a shows pooled results of flow cytometric analysis. PBMCs were gated for T cells and expression of activation markers CD69 and CD25 were evaluated. (Significances are indicated as follows: *p=0.05, p=0.001; n=4)

Figure 7B:
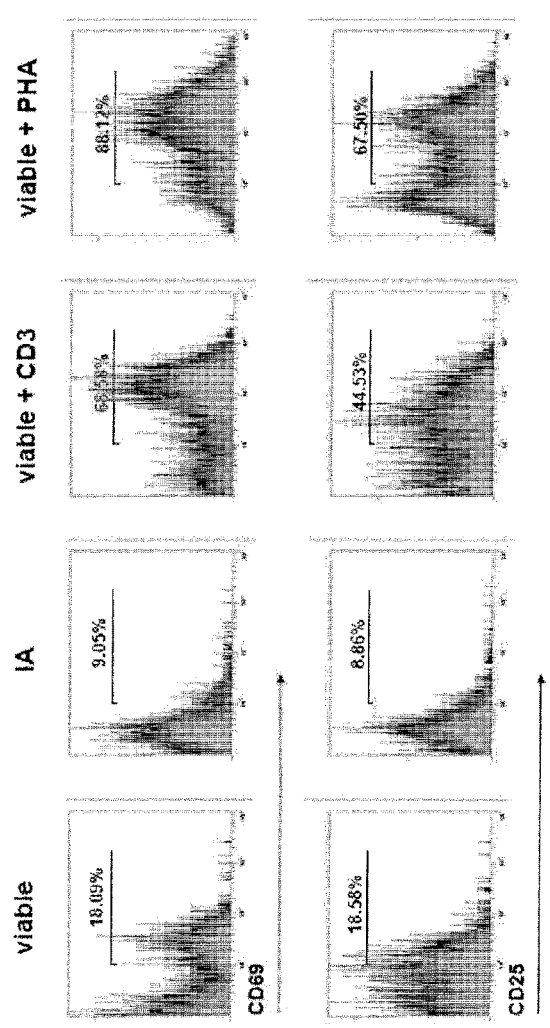
FIG. 7b displays a representative FACS analysis of PBMCs either activated (PHA, CD3 mAb). Gating represents % of positive cells.

FIG. 7b displays a representative FACS analysis of PBMCs either activated (PHA, CD3 mAb). Gating represents % of positive cells.

Figure 8:
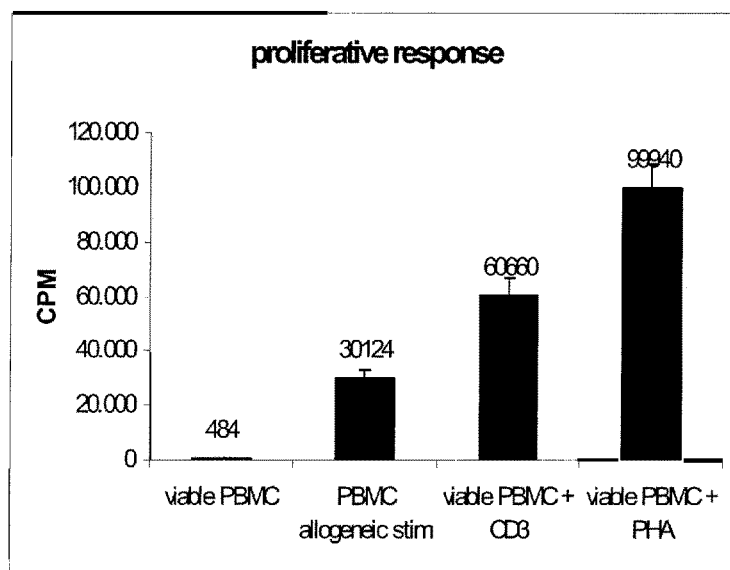
FIG. 8 shows high proliferation rates as measured by 3[H]-thymidine incorporation of stimulated PBMC when compared to viable PBMC cultured in RPMI without stimulation.

FIG. 8 shows high proliferation rates as measured by 3[H]-thymidine incorporation of stimulated PBMC when compared to viable PBMC cultured in RPMI without stimulation.

Figure 9:
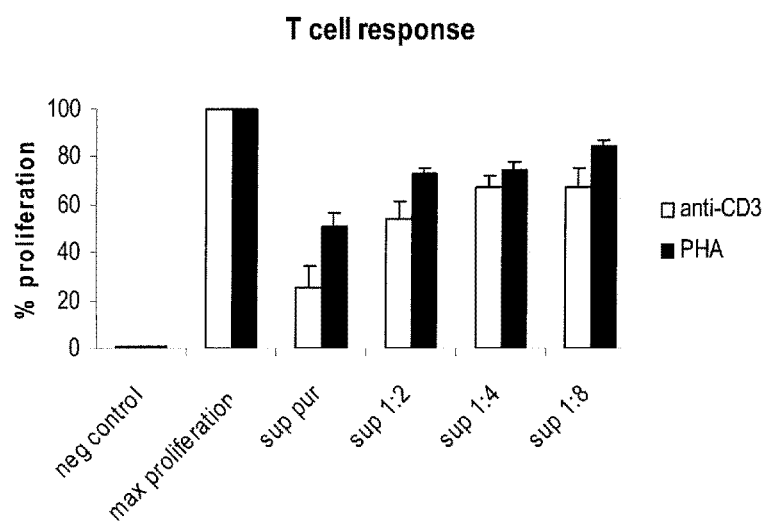
FIG. 9 shows inhibition of T cell response of PBMC secretoma in T cell proliferation assays.

FIG. 9 shows inhibition of T cell response of PBMC secretoma in T cell proliferation assays.

Figure 10:
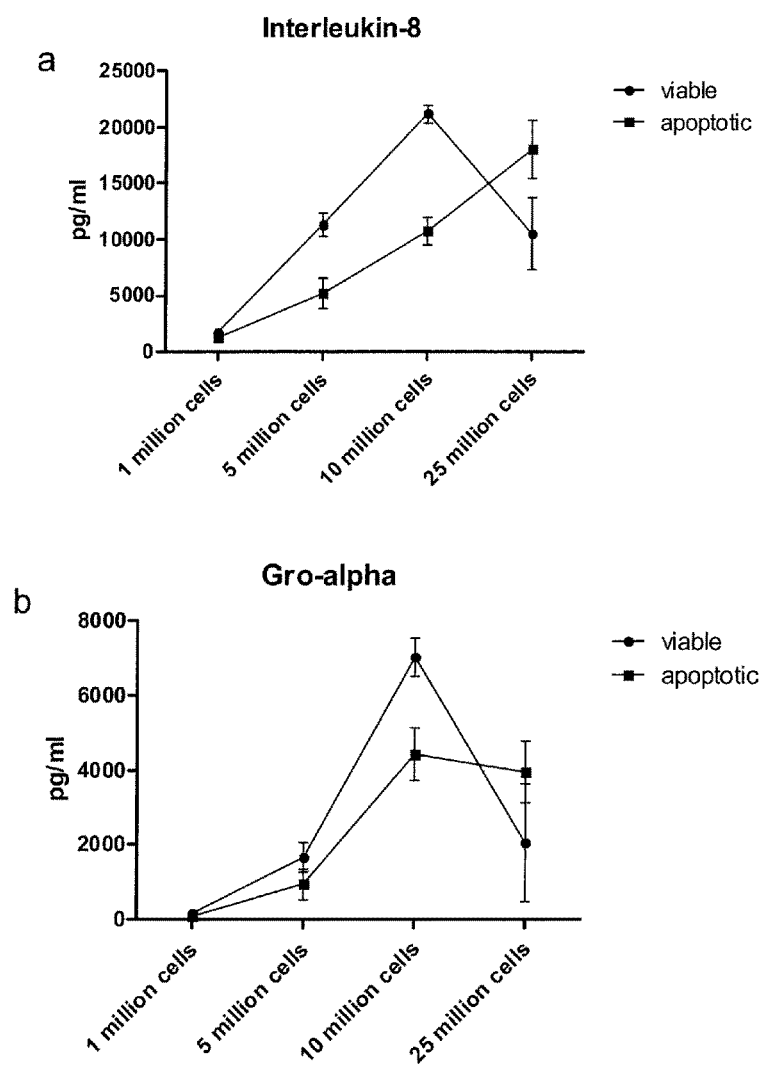
FIG. 10 a-f show supernatant levels of Interleukin-8, Gro-alpha, ENA-78, ICAM-1, VEGF and Interleukin-16.
Figure 10:
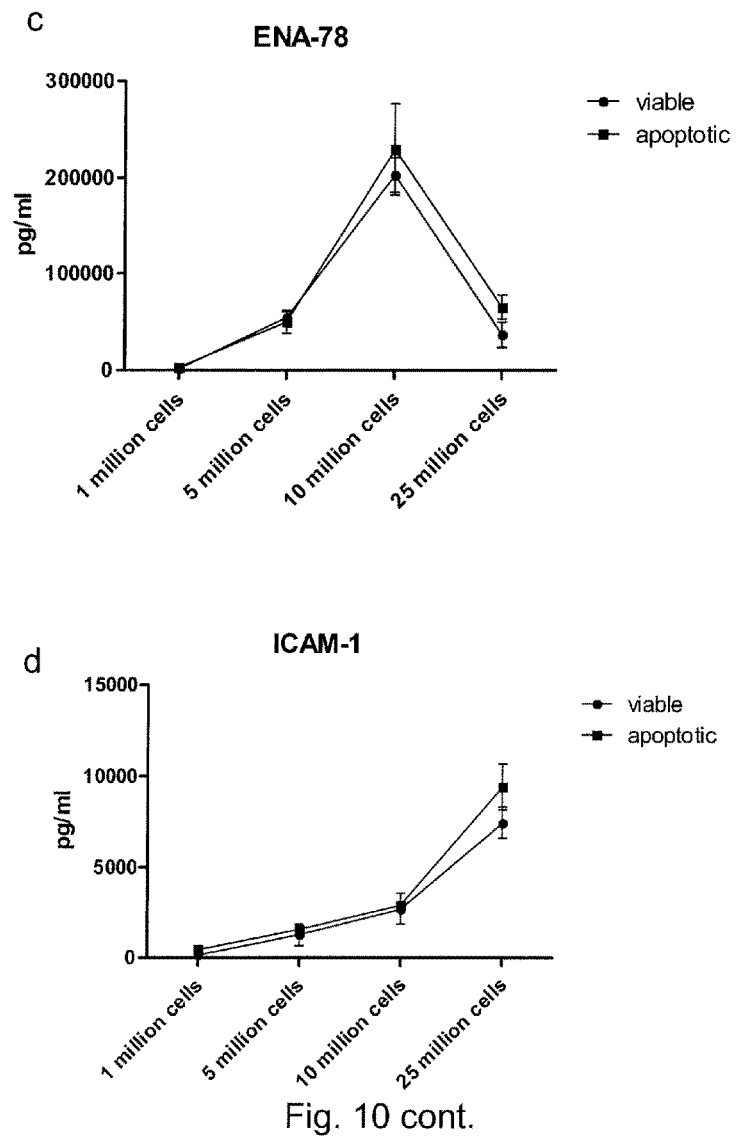
Figure 10:
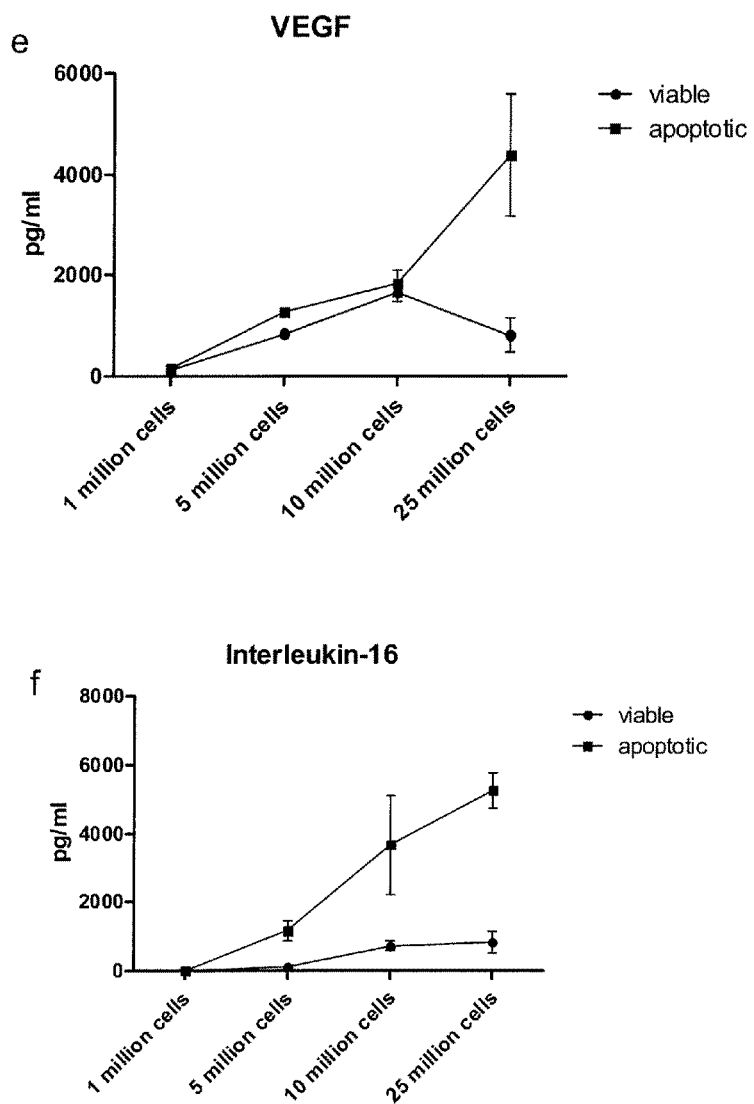

FIG. 10 (a-f) shows supernatant levels of Interleukin-8, Gro-alpha, ENA-78, ICAM-1, VEGF and Interleukin-16. Apoptotic PBMC show a markedly different secretion pattern of these cytokines and chemokime related to angiogenesis and immunesuppression compared to viable cells. This effect was even more pronounced when cells were incubated at high densities.

Figure 11:
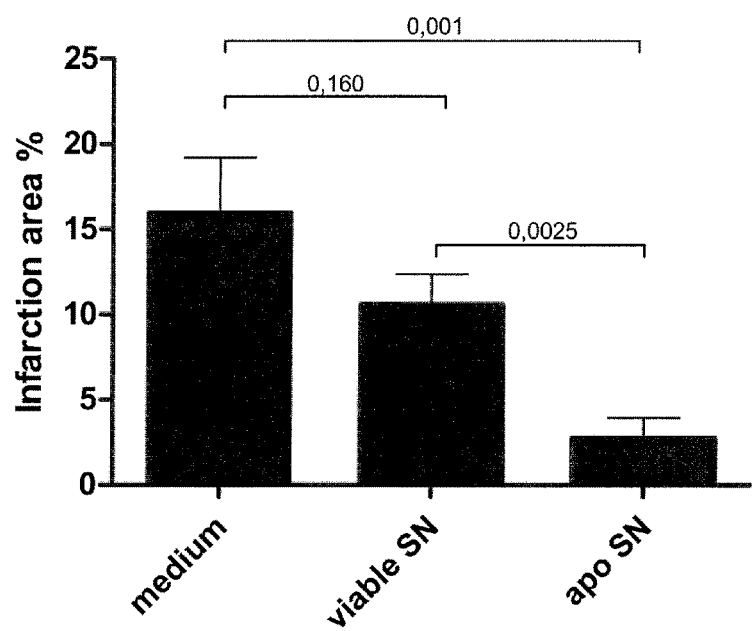
FIG. 11 shows the extension of myocardial scar tissue 6 weeks after experimental LAD ligation (as % of the left ventricle).

FIG. 11 shows the extension of myocardial scar tissue 6 weeks after experimental LAD ligation (as % of the left ventricle). Animals that were infused with cell culture supernatants derived from apoptotic cells evidence a significant reduction of collagene deposition, less scar extension and more viable myocardium.

Figure 12:
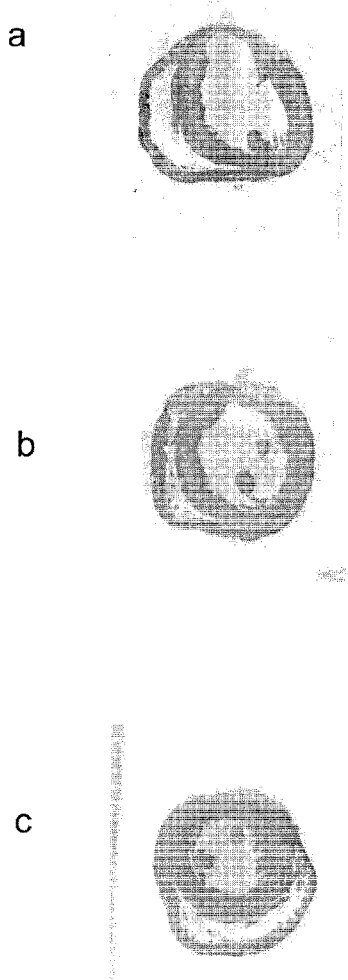
FIG. 12 a-c show macroscopic appearance of rat hearts explanted 6 weeks after experimental myocardial infarction.

FIG. 12 (a-c) shows macroscopic appearance of rat hearts explanted 6 weeks after experimental myocardial infarction. Animals transfused with supernatants from irradiated apoptotic cells (c) evidenced reduced collagen deposition and much smaller infracted areas compared to medium (a) or supernatants from viable cells (b). Scar tissue is coloured in green for better visualization.

Figure 13:
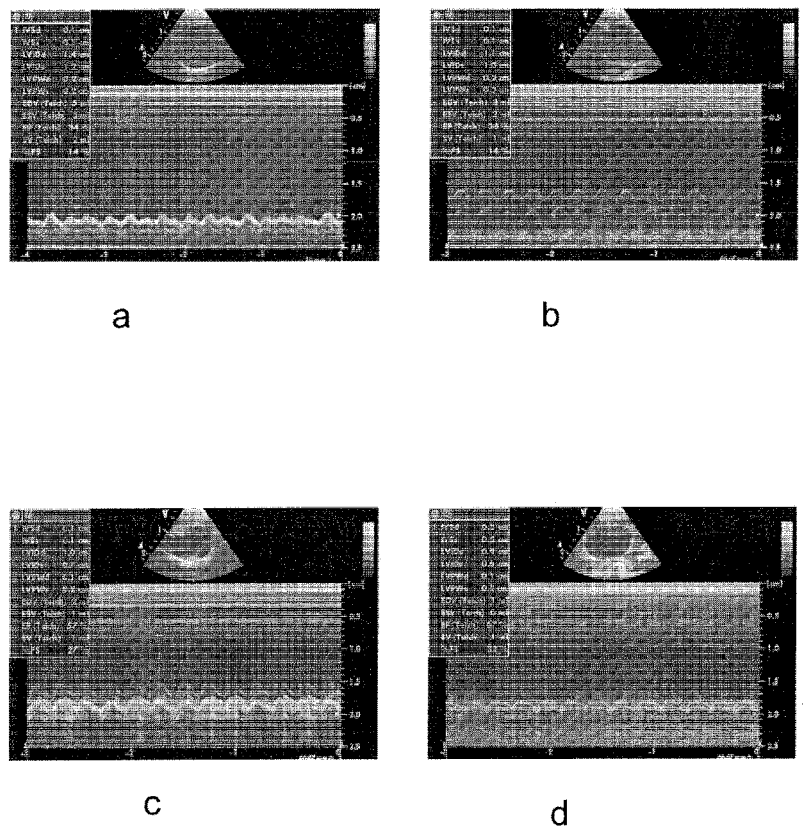
FIG. 13 a-d shows representative echocardiographic analyses (M-Mode).

FIG. 13 (a-d) shows representative echocardiographic analyses (M-Mode). Cardiac function was significantly better in rats transfused with IA-PBMC supernatants (c) compared to medium (a) and viable cell treated rats (b). Echocardiographic imaging from a sham operated rat is depicted in (d).

Figure 14:
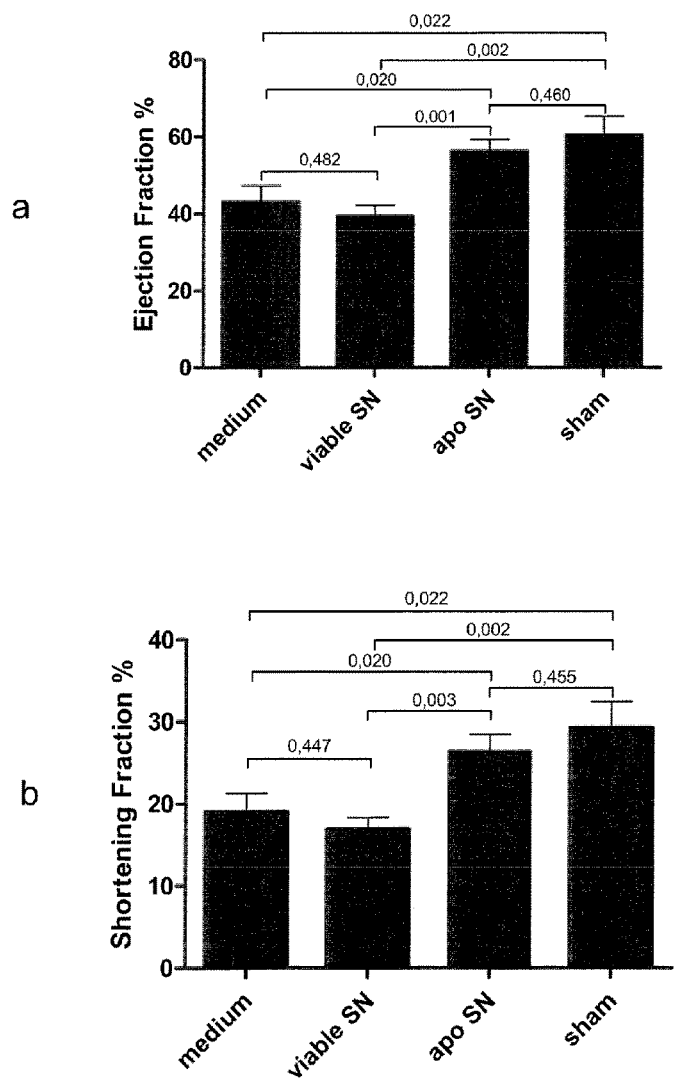
FIG. 14 a, and b show echocardiographic analyses conducted 6 weeks after myocardial infarction.

FIG. 14 (a, b) shows echocardiographic analyses conducted 6 weeks after myocardial infarction. Rats therapied with supernatants from irradiated apoptotic PBMC evidence a significantly better cardiac function compared to medium or viable cell culture supernatant infused animals.

Figure 15:
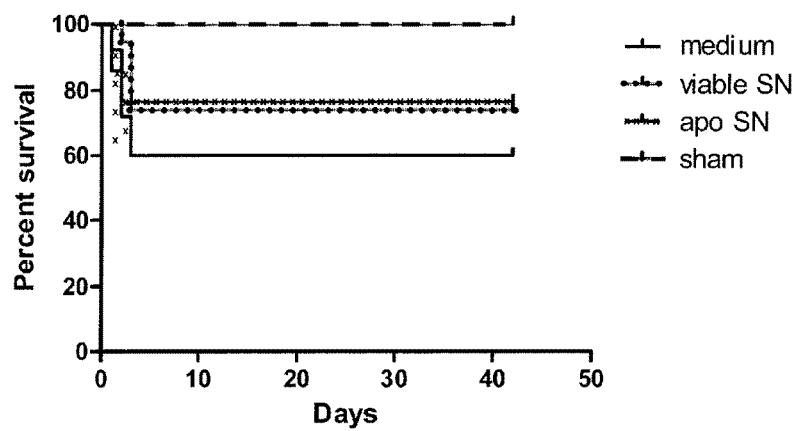
FIG. 15 shows Kaplan-Meier survival curve for all four treatment groups.

FIG. 15 shows Kaplan-Meier surivial curve for all four threatment groups. Both viable or apoptotic PBMC cell culture supernatant infused animals evidence a better survival compared to medium injected rats. (p<0.1).

Figure 16:
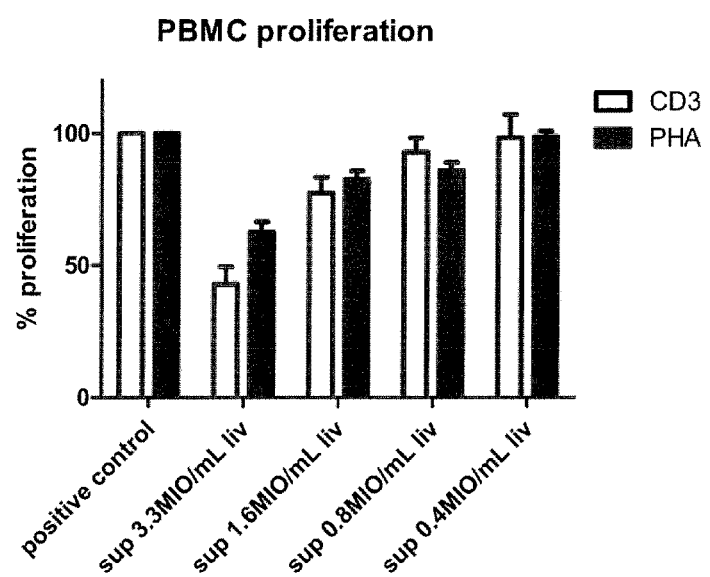
FIG. 16 shows anti-CD3 and PHA stimulation experiments performed with PBMC.

FIG. 16 shows anti-CD3 and PHA stimulation experiments performed with PBMC.

FIG. 17 shows the proliferation of PBMC upon stimulation with anti-CD3, PHA and mixed lymphocytes.

FIG. 18 shows the level of Annexin V and PI positivity of the supernatant of CD4+ cells inocubated with PBMC supernatants.

Figure 19:
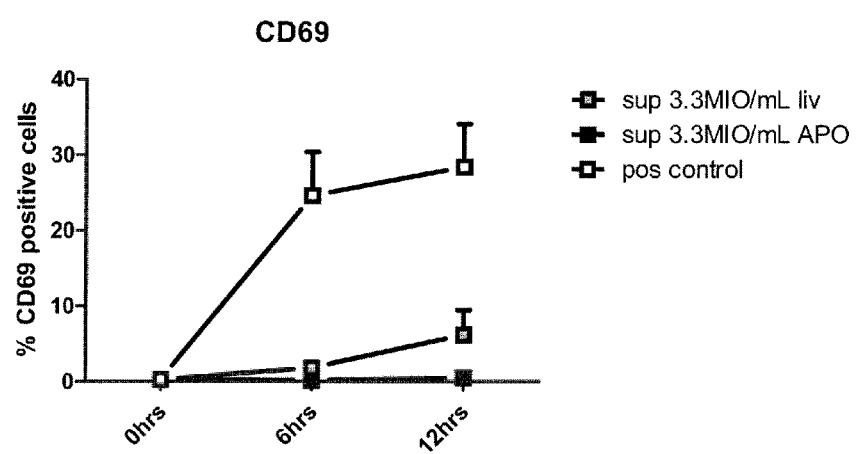
FIG. 19 shows the inhibition of the up-regulation of CD25 and CD69 in CD4+ cells by PBMC supernatant.

FIG. 19 shows the inhibition of the up-regulation of CD25 and CD69 in CD4+ cells by PBMC supernatant.

FIG. 20 shows that the demonetizing of IL-10 and TGF-β did not increase the proliferation rates of CD4+ cells.

EXAMPLES

Example 1

Acute myocardial infarction (AMI) often leads to congestive heart failure. Despite current pharmacological and mechanical revascularization no effective therapy is defined experimentally to replace infracted myocardium. Integral component of the remodelling process after AMI are the inflammatory response and the development of neo-angiogenesis after AMI. These processes are mediated by cytokines and inflammatory cells in the infarcted myocardium that phagocytose apoptotic and necrotic tissue and initiate homing of interstitial dendritic cells (IDC) and macrophages. Clinical trials aimed to attenuate AMI induced inflammatory response were abducted since systemic immune suppression (steroids) led to increased infarct size and delayed myocardial healing. From these data it was concluded that inflammatory response after AMI is responsible for tissue stabilization and scar formation. A new field in regenerative cardiovascular medicine emerged when investigators observed that distant stem cells sense sites of damage and promote structural and functional repair. By utilizing this approach, Orlic et al. injected c-kit positive endothelial progenitor cells (EPC) into the boarder zone of experimental AMI and increased neo-angiogenesis and regeneration of myocardial and vascular structures. This work ignited a plethora of publications that demonstrated a regenerative potential of "cell based therapy", however it still remains elusive whether this therapeutic effect is caused by the transplanted cells themselves, recruitment of resident cardiac stem cells, or by activation of, as yet, unidentified paracrine and immunologic mechanisms. Ischemia in infarcted myocardium causes apoptotic processes and initiates alterations of cell surface lipids on dying cells. The best-characterized modification is the loss of phospholipid asymmetry and exposure of phosphatidylserine (PS). These PS are recognized by macrophages and dendritic cells (antigen presenting cells, APC) via ligands such as thrombospondin, CD14 and CD36. Under physiological conditions these receptors serve to engulfe apoptotic and necrotic debris and initiate a silent "clean up" process. This process of phagocytosis by APC leads to a phenotypic anti-inflammatory response as determined by augmented IL-10 and TGF-β production and impaired APC function. Of clinical relevance are reports that demonstrated that infusion of apoptotic cells lead in a hematopoietic cell (HC) transplantation model to allogeneic HC engraftment and to a delay of lethal acute graft-versus-host disease (GVHD). Moreover, in solid organ transplantation models infusion of donor apoptotic cells increased heart graft survival. Contrary to inflammation and relevant to progenitor cell recruitment from bone marrow (BM) it was shown that opsonisation of apoptotic cells elicits enhanced VEGF and CXC8/IL-8 production of APC. In addition to the latter cytokines MMP9 was also identified to be vital for EPC recruitment and liberation from the bone marrow.

The current "status quo" in AMI treatment is directed toward early reperfusion and reopening the acute occluded coronary artery and that myocardial inflammation post infarction is perceived beneficiary despite this condition increases myocardial damage and counteracts endogenous repair mechanisms.

Material and Methods

Induction of Apoptosis of PBMC and Generation of Supernatants

For the in vivo experiments blood was drawn from healthy young volunteers. Apoptosis was induced by Cs-137 Caesium irradiation with 60 Gy (human PBMC) or with 45 Gy for in vivo (rat PBMC) experiments. Cells were resuspended in serum free Ultra Culture Medium (Cambrex Corp., USA) containing 0.2% gentamycin-sulfate (Sigma Chemical Co, USA), 0.5% β-mercapto-ethanol (Sigma, USA), 1% L-glutamin (Sigma, USA) and cultured in a humidified atmosphere for 24 h for in vitro experiments (concentration of cells, $1 \times 10^6$ ml). Induction of apoptosis was measured by AnnexinV-fluorescein/propidium iodide (FITC/PI) co-staining (Becton Dickinson, USA) on a flow cytometer. Annexin-positivity of PBMCs was determined to be >70% and are consequently termed IA-PBMC. Non-irradiated PBMC served as controls and are termed viable-PBMC. From both experimental settings supernatants were collected and served as experimental entities as described below (SN-viable-PBMC, SN-IA-PBMC).

LPS-Stimulation Experiments

Human PBMCs and monocytes (purity >95%) were separated using a magnetic bead system (negative selection Miltenyi Biotec, USA). PBMCs and monocytes were co-incubated for 4 h with different concentrations of apoptotic autologous PBMCs (annexin positivity >70%) and Lipopolysaccharide (1 ng/ml LPS; Sigma Chemical Co, USA). Supernatants were secured and kept frozen at −80° C. until further tests. IL-6 and IL-1β release was determined using commercially available ELISA kits (BenderMedSystems, Austria).

Monocyte-Derived DC Preparation and T-Cell Stimulation

PBMCs were isolated from heparinized whole blood of healthy donors by standard density gradient centrifugation with Ficoll-Paque (GE Healthcare Bio-Sciences AB, Sweden). T cells and monocytes were separated by magnetic sorting using the MACS technique (Miltenyi Biotec). Purified T cells were obtained through negative depletion of CD11b, CD14, CD16, CD19, CD33, and MHC class II-positive cells with the respective monoclonal antibody. Monocytes were enriched by using the biotinylated CD14 mAb VIM13 (purity 95%). DCs were generated by culturing purified blood monocytes for 7 days with a combination of GM-CSF (50 ng/ml) and IL-4 (100 U/ml). Subsequently, DCs were differently stimulated. Maturation was induced either by adding 100 ng/ml LPS from *Escherichia coli* (serotype 0127-B8, Sigma Chemie) for 24 h alone or by adding LPS for 2 h and further culturing the dendritic cells with apoptotic cells in a 1:1 ratio for 22 h. Additionally, DCs were treated with apoptotic cells alone (1:1) for 24 h. For the mixed leukocyte reaction (MLR), allogenic, purified T cells ($1 \times 10^5$/well) were incubated in 96-well cell culture plates (Corning Costar) with graded numbers of differently stimulated DCs for 6 days. The assay was performed in triplicate. Proliferation of T cells was monitored by measuring [methyl-3H]thymidine (ICN Pharmaceuticals) incorporation, added after 5 days. Cells were harvested after 18 h and incorporated [methyl-3H]thymidine was detected on a microplate scintillation counter.

Cell Culture, RNA Isolation and cDNA Preparation of Viable PBMC, IA-PBMC and SN Exposed Fibroblasts IA-PBMCs, viable-PBMC ($1 \times 10^6$ cells, both conditions cultured for 24 h in Ultra Culture Medium) and fibroblasts exposed to SN-viable-PBMC/SN-IA-PBMC were investigated ($1 \times 10^5$ fibroblasts obtained from Cascade Inc. (USA) were cultured in Dulbecco's modified Eagle medium (DMEM, Gibco BRL, USA) supplemented with 10% fetal bovine serum (FBS, PAA, Austria), 25 mM L-glutamine (Gibco, BRL, USA) and 1% penicillin/streptomycin (Gibco) and seeded in 12 well plates; fibroblasts were co-incubated with SN-viable-PBMC, SN-IA-PBMC for 4 and 24 h respectively). After RNA extraction of PBMC and fibroblasts (using RNeasy, QiIAGEN, Austria) following the manufacturer's instruction, cDNAs were transcribed using the iScript cDNA synthesis kit (BioRad, USA) as indicated in the instruction manual.

Quantitative Real Time PCR mRNA expression was quantified by real time PCR with LightCycler Fast Start DNA Master SYBR Green I (Roche Applied Science, Penzberg, Germany) according to the manufacturer's protocol. The primers for VEGF were: forward: 5'-CCCTGATGAGATCGAGTACATCTT-3' (SEQ ID NO: 1), reverse: 5'-ACCGCCTCGGCTTGTCAC-3' (SEQ ID NO: 2); for IL-8 forward: 5'-CTCTTGGCAGCCTTC-CTGATT-3' (SEQ ID NO: 3), reverse: 5'-TATGCACT-GACATCTAAGTTCTTTAGCA-3' (SEQ ID NO: 4); for MMP9 forward: 5'-GGGAAGATGCTGGTGTTCA-3' (SEQ ID NO: 5), reverse: 5'-CCTGGCAGAAATAG-GCTTC-3'_(SEQ ID NO: 6) and for β-2-microglobulin β 2M, forward: 5'-GATGAGTATGCCTGCCGTGTG-3'_ (SEQ ID NO: 7), reverse: 5'-CAATCCAAATGCG-GCATCT-3' (SEQ ID NO: 8). The relative expression of the target genes was calculated by comparison to the house keeping gene β2M using a formula described by Wellmann et al. (Clinical Chemistry. 47 (2001) 654-660, 25). The efficiencies of the primer pairs were determined as described (A. Kadl, et al. Vascular Pharmacology. 38 (2002) 219-227).

Release of Pro-Angiogenetic Factors and MMP9 by Viable PBMC and IA-PBMC After Culture IA-PBMC ($5*10^5$) and viable PBMC were incubated in a humidified atmosphere for 24 h. Supernatants were collected after 24 h and immediately frozen at −80° C. until evaluation. Lysates of respective cells served as controls. Release of pro-angiogenetic factors (VEGF-A, CXCL-8/IL-8, GMCSF, GCSF) and MMP9, an accepted liberating factor of c-kit cells, were analysed utilizing ELISA (R&D, USA) following the manufacturer's instructions. Plates were read at 450 nm on a Wallac Multilabel counter 1420 (PerkinElmer, USA).

Acquisition of Syngeneic IA-PBMC and Viable-PBMC for AMI in vivo Experiment

Syngeneic rat PBMC for in vivo experiments were separated by density gradient centrifugation from whole-blood obtained from prior heparinized rats by punctuation of the heart. Apoptosis was induced by Cs-137 Caesium irradiation with 45 Gy for in vivo experiments and cultured for 18 h as described above. (annexin staining >80% IA-PBMC, annexin staining <30% viable PBMC, $1\times10^6$/ml).

Induction of Myocardial Infarction

Myocardial infarction was induced in adult male Sprague-Dawley rats by ligating the LAD as previously described (Trescher K, et al. Cardiovasc Res. 2006: 69(3): 746-54). In short, animals were anesthetized intraperitoneally with a mixture of xylazin (1 mg/100 g bodyweight) and ketamin (10 mg/100 g bodyweight) and ventilated mechanically. A left lateral thoracotomy was performed and a ligature using a 6-0 prolene was placed around the LAD beneath the left atrium. Immediately after the onset of ischemia $8\times10^6$ apoptotic PBMCs suspended in 0.3 ml cell culture medium were infused through the tail vein. Infusion of cell culture medium alone, viable PBMC and sham operation respectively or served in this experimental setting as negative control. The rat experimental design is shown in FIG. 1 (FIGS. 1a, b).

Tracking of Apoptotic Cells $8\times10^6$ syngeneic rat PBMC were labelled with 15 μM Carboxy-fluorescein diacetate succinimidyl ester (CFSE, Fluka Bio-Chemika, Buchs, Switzerland) at room temperature for 10 min. Labelling was stopped by the addition of fetal calf serum (FCS). Apoptosis was induced (annexin V>70%) and cells were injected after ligation procedure. 72 h after operation rats were sacrificed and liver, spleen and heart were processed following a standard procedure for frozen sections (n−4). Samples were analyzed by confocal laser scanning microscopy (ZEISS LSM 510 laser scanning microscope, Germany) as described previously (Kerjaschki D, J Am Soc Nephrol. 2004; 15: 603-12).

Histology and Immunohistochemistry in vivo

All animals were sacrificed either 72 h or 6 weeks after experimental infarction. Hearts were explanted and then sliced at the level of the largest extension of infarcted area (n=8-10). Slices were fixed with 10% neutral buffered formalin and embedded in paraffin for (immune-)histological staining. The tissue samples were stained with hematoxylin-eosin (H&E) and elastic van Gieson (evg). Immunohistological evaluation was performed using the following antibodies directed to CD68 (MCA 341R, AbD Serotec, UK), VEGF (05-443, Upstate/Milipore, USA), Flk-1 (sc-6251, Santa Cruz Biotechnology, USA), CD34 (sc-52478, Santa Cruz Biotechnology, USA), c-kit (sc-168, Santa Cruz Biotechnology, USA), S100 beta (sc-58841, Santa Cruz Biotechnology, USA). Tissue samples were evaluated on a Olympus Vanox AHBT3 microscope (Olympus Vanox AHBT3, Olympus Optical Co. Ltd., Japan) at 200× magnification and captured digitally by using a ProgRes Capture-Pro C12 plus camera (Jenoptik Laser Optik Systeme GmbH, Germany).

Determination of Myocardial Infarction Size by Planimetry

In order to determine the size of the infarcted area, Image J planimetry software (Rasband, W. S., Image J, U. S. National Institutes of Health, USA) was used. The extent of infarcted myocardial tissue (% of left ventricle) was calculated by dividing the area of the circumference of the infarcted area by the total endocardial and epicardial circumferenced areas of the left ventricle. Planimetric evaluation was carried out on tissue samples stained with evg for better comparison of necrotic areas. Infarct size was expressed as percent of total left ventricular area.

Cardiac Function Assessment by Echocardiography

Six weeks after induction of myocardial infarction rats were anaesthetized with 100 mg/kg Ketamin and 20 mg/kg Xylazin. The sonographic examination was conducted on a Vivid 5 system (General Electric Medical Systems, USA). Analyses were performed by an experienced observer blinded to treatment groups to which the animals were allocated (EW). M-mode tracings were recorded from a parasternal short-axis view and functional systolic and diastolic parameters were obtained. Ventricular diameters and volumes were evaluated in systole and diastole. Fractional shortening was calculated as follow: FS (%)=((LVEDD−LVESD)/LVEDD)*100%

Statistical Methods

Statistical analysis was performed using SPSS software (SPSS Inc., USA). All data are given as mean±standard of the mean. Normal distribution was verified using the Kolmogorov-Smirnov test. Paired two-sided t-tests for dependent, unpaired t-tests for independent variables were utilized calculating significances. Bonferroni-Holm correction was used to adjust p-values for multiple testing. P-values <0.05 were considered statistically significant.

Results

Induction of Apoptosis with Caesium Irradiation (IA-PBMC)

In order to evaluate the immunomodulatory potential of apoptotic cells, first the cellular response to induction of apoptosis by caesium irradiation of human peripheral blood mononuclear cells (PBMC) was determined by flow cytometry utilizing Annexin-V/PI staining on a flow cytometer. Irradiation caused positivity for Annexin on PBMC in a time dependent manner and peaked within 24 h as compared to viable PBMC. Viable cells served as controls (FIG. 2a). Since Annexin-V binding was highest after 24 h all further in vitro investigations were performed after this culture period (IA-PBMC). Viable PBMC served in RT-PCR and supernatant experiments as control.

IA-PBMC Evidence Immune Suppressive Features in vitro

Interleukin-1β and IL-6 is recognized as the predominant pro-inflammatory mediator in myocardial infarction in vivo. To test the hypothesis whether IA-PBMC has an effect on cellular response human monocytes and PBMC were co-incubated with IA-PBMC and target cells were stimulated with LPS. A dose dependent decrease in secretion of IL-1β and IL-6 in cultures of both cell types as evaluated by ELISA was found (FIGS. 2b, c). To verify anti-proliferative effects of IA-PBMC in an allogeneic model a mixed lymphocyte reaction (MLR) was utilized. Allogenic, purified T-cells were utilized and these effector cells were incubated with graded doses of dendritic cells with/without addition of IA-PBMC. FIG. 2d evidences that co-incubation of IA-PBMC decreases proliferation rate in a dose-dependent manner.

IA-PBMC and Viable PBMC Evidence Increased mRNA Transcription of VEGF, IL-8/CXL8, and MMP9

To substantiate whether irradiation leads to enhanced mRNA transcription of proteins known to be related to mobilization of EPC PBMC was analysed after separation, and after apoptosis induction (24 h). Viable PBMC served as control (viable PBMC or IA-PBMC). RNA transcription showed little difference VEGF expression as determined by RT-PCR, however a strong enhancement of IL-8/CXCL8 and MMP9. Peak induction for IL-8/CXL8 in IA-PBMC was 6 fold versus 2 fold in viable cells, and 30 fold versus 5 fold for MMP9, respectively (FIG. 2e).

IA-PBMC and Viable PBMC Secrete Paracrine Factors that Cause Endothelial Progenitor Cells (EPC) Liberation SN derived from IA-PBMC and viable PBMC were quantified for VEGF, IL-8/CXCL8, GMCSF, GCSF and MMP9 utilizing ELISA after 24 h culture. As seen in FIG. 2f VEGF, IL-8/CXCL8 and MMP9 evidenced an increment. GM-CSF and G-CSF were not detectable. Of interest was the finding that MMP9 evidenced peak values in cell lysates.

SN Derived from IA-PBMC and Viable PBMC Augment Pro-Angiogenic mRNA Transcription in Mesenchymal Fibroblasts Since stromal cells in bone marrow are constitutively fibroblasts it was sought to investigate whether co-incubation of fibroblasts with SN derived from IA-PBMC and viable PBMC had the ability to increase VEGF, IL-8/CXCL8 and MMP9 mRNA transcription, factors responsible for EPC mobilization. RT-PCR was conducted at 4 and 24 h. Highest levels of induction were detected for IL-8/CXCL8 in cells cultivated in IA-PBMC SN, reaching an almost 120-fold induction at 4 h as compared to control. This response is also present at 24 h. A comparable response was found for VEGF, whereas MMP9 upregulation was predominantly found after 24 h. This data indicates that SN contains paracrine factors that enhance fibroblasts to augment mRNA products responsible for pro-angiogenic effects in the BM (FIG. 2g).

Adoptive Transfer of CFSE Labelled IA-PBMC in a Rat Myocardial Infarction Model

Because it could be proven that cultured IA-PBMC are both anti-inflammatory and pro-angiogenic in vitro IA-PBMC and viable PBMC were infused in an acute rat AMI model. First it was sought to determine where these cultured cells are homing after infarction. CFSE labelled IA-PBMC were injected into the rat's tail vein shortly after LAD artery ligation. A representative histology is seen in FIGS. 3a, b, c. The majority of CFSE IA-PBMC were trapped in the spleen and liver tissue within 72 h. No cells were observed in the heart.

Diverted Early Inflammatory Immune Response in IA-PBMC Treated AMI

Upon closer investigation in H.E. staining, control infarction and viable leucocytes (viable PBMC) treated AMI rats evidenced a mixed cellular infiltrate in the wound areas in accordance to granulation tissue with abundance of neutrophils, macrophages/monocytes, lymphomononuclear cells, fibroblasts and activated proliferating endothelial cells admixed to dystrophic cardiomyocytes (FIGS. 3d, e) within 72 h after AMI. In contrast, AMI rats treated with IA-PBMC evidenced a dense monomorphic infiltrate in wound areas that consisted of medium sized monocytoid cells with eosinophilic cytoplasm, dense nuclei and a round to spindle shaped morphology (FIG. 3f). In addition, few lymphomononuclear cells, especially plasmacells, fibroblasts and endothelial could be detected. Immunohistochemical analysis revealed that the cellular infiltrate in IA-PBMC AMI rats was composed of abundant CD68+ monocytes/macrophages (FIG. 3i) that were much weaker in the other two groups (MCI, Viable PBMC, IA-PBMC, high power field, HPF, 60.0±3.6, 78.3±3.8, 285.0±23.0 (SEM), respectively) (FIGS. 3g, h). Content on Vimentin positive mesenchymal cells was similar in all groups while S100+ dendritic cells were preferentially found in control infarction (AMI, Viable PBMC, IA-PBMC, HPF 15.6±1.7, 12.4±2.3, 8.4±1.2 (SEM), respectively as compared to treated groups (FIGS. 3j, k, h Representative histology, n=5)).

Early Homing of VEGF+, Flk1+ and c-Kit+ Cells in IA-PBMC Treated AMI

Since IA-PBMC evidenced a dense monomorphic infiltrate in wound areas that consisted of medium sized monocytoid cells with eosinophilic cytoplasm and dense nuclei multiple surface markers related to neo-angiogenesis and regenerative potency were explored. This cell population identified in the H.E. staining in IA-PBMC treated AMI group stained highly positive for vascular endothelial growth factor (VEGFa), Flk-1 and c-kit (CD 117) (FIGS. 4c, f, i). Expression of both markers was reduced in control AMI and viable PBMC treated AMI group (FIGS. 4a, b, d, e, j). Interestingly, IA-PBMC treated AMI evidenced increased CD34+ cells within the densely populated infarcted area which is attributed to vascular structure putatively referring to colonisation of 34+ cells (I) as compared to control (G, H) (Representative histology, n=5)

Attenuated Infarct Size in IA-PBMC Treated AMI

In a planimetric analysis performed on EVG stained tissue samples from hearts explanted 6 weeks after myocardial infarction was induced, rats receiving saline show a collagenous scar extending to over 24.95%±3.58 (SEM) of the left ventricle with signs of dilatation. In IA-PBMC treated rats these signs were almost abrogated with infarct sizes of 5.81%±2.02 (SEM) as compared to 14.3%±1.7 (SEM) treated with viable PBMC (FIGS. 5a,b,c).

LV Function Improves in IA-PBMC Treated AMI

Intravenous application of syngeneic cultured IA-PBMC significantly improves echocardiographic parameters as compared with viable PBMC or culture medium treated animals. Shortening fraction (SF) evidenced values of 29.16%±4.65 (SEM) in sham operated animals, 18.76%±1.13 (SEM) in medium treated AMI animals, 18.46%±1.67 (SEM) in the viable PBMC AMI group and 25.14%+2.66 (SEM) in IA-PBMC treated rats (FIG. 5e). Ejection fraction (EF) was 60.58%±6.81 (SEM) in sham operated rats and declined to 42.91%12.14 (SEM) in AMI animals treated with medium, and to 42.24%±3.28 (SEM) in animals receiving viable PBMC, whereas rats treated with IA-PBMCs evidenced a EF of 53.46%±4.25.

Analysis of end-systolic and end-diastolic diameters (LVESD, LVEDD), end-systolic and end-diastolic volumes (LVESV, LVEDV) showed a comparable pattern to the previously observed values. Saline receiving animals and viable PBMC treated rats showed LVEDD values of 10.43 mm±0.21 (SEM) and 11.03 mm±0.40 respectively, IA-PBMC rats even represented a slighty reduced left-ventricular diastolic diameter of 8.99 mm±0.32 compared to 9.47 mm±0.64 in sham operated animals. Differences in systolic diameters were less pronounced, but in the same ranking (Panel 5 (a, b, c)

Conclusion:

These findings demonstrate that irradiated apoptotic PBMC (IA-PBMC) induces immune suppression in vitro and is associated to secretion of pro-angiogenic proteins. Therefore cultured viable-PBMC and IA-PBMC were infused in an acute rat AMI model and demonstrated that this treatment evoked massive homing of FLK1+/c-kit+ positive EPC into infarcted myocardium within 72 h and caused a significant functional recovery within 6 weeks.

Co-culture of IA-PBMC in immune assays resulted in reduced IL-1β and IL-6 production and attenuated allogeneic dendritic mixed lymphocyte reaction (MLR). Both immune parameters were described to have a role in inflammation after myocardial ischemia. In addition, it was evidenced that viable- and IA-PBMC secrete CXCL8/IL-8 and MMP9 into the culture medium within 24 h. These proteins were described to be responsible for neo-angiogenesis and recruitment of EPC from the BM to the ischemic myocardium. The CXCL8/IL-8 chemokine belongs to the CXCL family that consists of small (<10 kDa) heparin-binding polypeptides that bind to and have potent chemotactic activity for endothelial cells. Three amino acid residues at the N-terminus (Glu-Leu-Arg, the ELR motif) determine binding of CXC chemokines such as IL-8 and Gro-alpha to CXC receptors 1 and 2 on endothelial cells and are promoting endothelial chemotaxisis and angiogenesis. In addition MMP9 secretion was identified to be pivotal in EPC mobilisation since this matrixproteinase serves as signal to release soluble kit-ligand (sKitL), a chemokine that causes the transition of endothelial and hematopoietic stem cells (EPC) from the quiescent to proliferative niche in the BM. In a further in vitro assay it could be demonstrated that the supernatant (SN) derived from cultured viable- and IA-PBMC had the ability to enhance mRNA transcription of CXCL8/IL-8 and MMP9 in mesenchymal fibroblasts. These data indicate that SN derived from viable and irradiated PBMC contain paracrine factors that confer a biological situation in the BM which results in elution of c-kit+ EPC into circulation.

In order to prove any beneficial effect of this culture-cell suspension in vivo a model of open chest myocardial injury and infused cultured viable- and IA-PBMC shortly after LAD ligation in rat animal model was utilized. In a first attempt it was proved that CSFE labelled IA-PBMC were trapped in majority in the spleen and the liver. These data indicate that "cell based therapy" does not home in infarcted myocardium. In contrary, it is much more likely that paracrine effects, either by "modified" culture medium alone or by evoked "immune mediated cytokine storm" due to cell-culture suspension exposure is causative for the regenerative effect in AMI. Since immediate inflammation after acute ischemia determines the road map to ventricular dilatation histological analysis after 72 h after AMI was performed. It could be shown that IA-PBMC treated rats evidenced massive homing of CD68+ and VEGFa/FLK1/c-kit+ positive EPC cell populations within this time period. In contrast, more S100 β positive dendritic cells were found in control AMI, indicating enhanced APC based inflammation in control AMI.

The results seen in IA-PBMC treated rats partly foil currently accepted knowledge about the natural course of myocardial infarction. In regards to inflammation: Under normal conditions remodeling processes are mediated by cytokines and inflammatory cells in the infarcted myocardium that initiate a wound reparation process that is landmarked by phagocytosis and resorbtion of the necrotic tissue, hypertrophy of surviving myocytes, angiogenesis and, to a limited extent, progenitor cell proliferation. Any experimental approach so far that intervened into inflammatory response post infarction was shown to be detrimental in AMI models. When interpreting the present histological short term data it is argued that IA-PBMC cell-medium suspension in AMI results in an advanced transitioning from inflammation to c-kit+ EPC repair phase. Previous work has confirmed that bone marrow of circulating progenitor cell therapy after AMI improve cardiac function, regardless of whether transdifferentiation of the cells to cardiomyocytes occurs or does not. In regard to c-kit+ EPC the bone marrow derived cells are considered as having a significant role as indispensable for cardiac repair. Pharmacological inhibition with imatinib mesylate and non-mobilization of c-kit+ EPC resulted in an attenuated myofibroblast response after AMI with precipitous decline in cardiac function.

These results show the regenerative potency of infusing "syngeneic" cultured IA-PBMC in patients suffering from AMI and indicate that patients who suffer from acute AMI would benefit from being transfused with autologous (=from the patient to be treated or from the same species) IA-PBMC.

Example 2

Resting Peripheral Blood Mononuclear Cells (PBMC) Evidence Low Activation Marker and Reduced Inflammatory Cytokine Production Activated peripheral blood mononuclear cells (PBMCs) and their supernatants (SN) are supposed to be beneficial in wound regeneration (Holzinger C et al. Eur J Vasc Surg. 1994 May; 8(3): 351-6.). In example 1 it could be shown that non-activated PBMC and SN derived thereof has beneficial effects in an experimental acute myocardical infarct (AMI) and wounding model. Since non-activation of PBMC had to be verified experimentally it was investigated whether cultivation of PBMC leads to enhanced T-cell activation markers (CD69, CD25) or enhanced inflammatory cytokine secretion (monocyte activation=TNFα, T-cell activation=INFγ). In a control experiment cultured T cells were triggered by CD3 mAb stimulation or Phytohemagglutinin (PHA).

Methods and Results

Venous blood was collected in EDTA-tubes from healthy volunteers. After Ficoll-Hypaque density grade separation, PBMC were collected and divided into viable and irradiated apoptotic cells (IA-PBMC). To obtain apoptotic cells, PBMC were irradiated with 60 Gy (Caesium-137). For flow cytometric analysis 500,000 PBMC were cultivated in 200 μl serum-free medium. Cells were either stimulated with PHA (7 μg/mL) or CD3-mAb (10 μg/mL) or were left unstimulated. After 24 h of incubation cells were washed, stained for CD3, CD69 and CD25 (R&D System) and evaluated for surface activation markers on a FC500 (Coulter). For ELISA assays PBMC were cultivated overnight at a density of $2.5 \times 10^6$ cells/ml, either with or without PHA or CD3 stimulation. After 24 h supernatants were harvested and frozen at −20° C. Commercially available ELISA kits for TNF-α (R&D) and INF-γ (Bender) were purchased. In short, MaxiSorp plates were coated with antibodies against INF-α and INF-γ and stored overnight. After 24 h, plates were washed and samples added in duplicates to each well. After incubation and addition of a detection antibody and Streptavidin-HRP, TMB-substrate was added to each well. After color development, the enzymatic reaction was stopped by addition of sulphic acid. Optical density values were read on a Wallac Victor3 plate reader.

Results:

FACS analysis: CD3 and PHA stimulated T cells showed an upregulation of activation markers CD69 and CD25 after 24 h of incubation. Unstimulated and apoptotic cells expressed only low amounts of CD69 and CD25 (FIG. 6a (representative sample, FIG. 6b, histogram, n=4). Statistical significance is indicated by asterix (xx $p<0.001$, x $p<0.05$). ELISA analysis: Whereas neither TNF-α and INF-γ in unstimulated PBMC-derived supernatants were detected, supernatants from PHA or CD3 stimulated PBMC evidenced high values for these cytokines as indicated by ELISA analysis (asterix **$p<0.001$, *$p<0.05$, n=8). The results clearly show a different secretion pattern of inflammatory cytokines in comparison to unstimulated PBMC.

Conclusion:

These data indicate that "unstimulated PBMC" evidence a distinct different phenotype (activation marker, cytokine secretion) as compared to stimulated PBMCs (PHA and CD3 mAb).

FIG. 6a indicates that neither unstimulated viable PBMC or IA-PBMC secrete the mainly monocyte derived pro-inflammatory cytokine TNF-α. (Significances are indicated as follows: *p–0.05, **p=0.001n=8)

FIG. 6b demonstrates a strong induction of pro-inflammatory Interferon-γ secretion after activation as compared to unstimulated PBMC. (Significances are indicated as follows: *p=0.05, **p=0.001; n=8)

FIG. 7a shows pooled results of flow cytometric analysis. PBMCs were gated for T cells and expression of activation markers CD69 and CD25 were evaluated. (Significances are indicated as follows: *p–0.05, **p–0.001; n–4)

FIG. 7b displays a representative FACS analysis of PBMCs either activated (PHA, CD3 mAb). Gating represents % of positive cells.

Example 3

Proliferative Activity of PBMC Cultivated in a Physiological Solution

The aim of this example is to prove that PBMC have no proliferative activity as compared to immune assays that utilize specific (CD3), unspecific (lectin, PHA) and allogeneic T-cell triggering (mixed lymphocyte reaction, MLR) in a 2 day (CD3, PHA) and 5 day (MLR) stimulation assay.

Material and Methods

PBMC were separated from young healthy volunteers by Ficoll density gradient centrifugation and resuspended in RPMI (Gibco, USA) containing 0.2% gentamycinsulfate (Sigma Chemical Co, USA), 1% L-Glutamin (Sigma, USA) at $1*10^5$ cells per 200 µL. Responder cells were either stimulated by MoAb to CD3 (10 µg/mL, BD, NJ, USA), PHA (7 µL/mL, Sigma Chemical Co, USA) or with irradiated allogeneic PBMC at a 1:1 ratio (for MLR). Plates were incubated for 48 h or 5 days and then pulsed for 18 h with 3[H]-thymidine ($3.7*10^4$ Bq/well; Amersham Pharmacia Biotech, Sweden). Cells were harvested and 3[H]-thymidine incorporation was measured in a liquid scintillation counter.

Results

Stimulated PBMC showed high proliferation rates as measured by 3[H]-thymidine incorporation when compared to viable PBMC cultured in RPMI without stimulation (FIG. 8). This effect was observed by adding T cell specific stimuli (PHA, CD3) as well as in assays where proliferation was triggered by antigen presenting cells (MLR).

Conclusion

This set of experiments implicates that viable PBMC held in culture for up to 5 days did not proliferate whereas PBMC stimulated by different ways showed a marked proliferative response. It is concluded that culture of PBMC without stimulation does not lead to proliferative response.

Example 4

Secretoma of Separated PBMC Kept Under Sterile Culture Conditions Possess Neo-Angionetic Capacity Since neo-angionesis and inflammation are strongly linked in vivo it was investigated whether these secretoma of PBMC also exhibit anti-proliferative effects on T cells and therefore interfere with an inflammatory immune response.

Material and Methods

Secretoma were obtained by incubating PBMC ($2.5*10^6$/mL) from young healthy volunteers separated by Ficoll density gradient centrifugation for 24 h in RPMI (Gibco, CA, USA) containing 0.2% gentamycinsulfate (Sigma Chemical Co, USA), 1% L-Glutamine (Sigma, USA). Supernatants were separated from the cellular fraction and stored at −80° C. For proliferation assays allogeneic PBMC were resuspended at $1*10^5$ cells per 200 µL RPMI after separation. Responder cells were either stimulated by MoAb to CD3 (10 µg/mL, BD, USA) or PHA (7 µL/mL, Sigma Chemical Co, USA). Different dilutions of supernatants were added. Plates were incubated for 48 h and then pulsed for 18 h with $^3$[H]-thymidine ($3.7*10^4$ Bq/well; Amersham Pharmacia Biotech, Sweden). Cells were harvested and $^3$[H]-thymidine incorporation was measured in a liquid scintillation counter.

Results:

Secretoma of allogeneic PBMC evidenced a significant reduction of proliferation rates measured by $^3$[H]-thymidine incorporation when compared to positive controls (FIG. 9). This effect was dose-dependent and could be seen upon anti-CD3 as well as upon PHA stimulation.

Implication:

This set of experiments implicates that secretoma obtained from viable PBMC held in culture for 24 h exhibit significant anti-proliferative effects in vitro. These data indicate that supernatant derived from PBMC or in lyophilised form may serve as potential therapeutic formula to treat human diseases that are related to hypoxia induced inflammation or other hyperinflammatory diseases (e.g. auto-immune diseases, inflammatory skin diseases).

Example 5

Paracrine Factors Secreted by Peripheral Blood Mononuclear Cells Preserve Cardiac Function In example 1 it was shown that transfusion of cultured irradiated apoptotic cells derived from peripheral blood significantly improved functional cardiac recovery after experimental myocardial infarction in rats. This improvement was based on immunesuppressive features of apoptotic cells, pro-angiogenic effects and induction of augmented homing of c-kit+ endothelial progenitor cells (EPCs).

In the present example peripheral blood mononuclear cells (PBMC) either viable or irradiated with a dose of 60 Gray were incubated for 24 hours to generate conditioned cell culture supernatants. Supernatants were lyophilized and kept frozen until use in in vivo experiments. Myocardial infarction was induced in Sprague-Dawley rats by ligating the left anterior descending artery. After the onset of ischemia, lyophilized supernatants were resuspended and injected intravenously. Tissue samples for histological and immunehistological evaluations were obtained three days and six weeks after myocardial infarction. Cardiac function was assessed by echocardiography six weeks post AMI. Sham operated and untreated animals served as controls.

Rats that were infused with supernatants obtained from apoptotic PBMC evidenced increased myocardial angiogenesis and enhanced homing of endothelial progenitor cells within 72 hours as compared to controls. Planimetric evaluation of fibrotic areas indicated reduced infarction size in animals treated with supernatants from apoptotic cells. Furthermore, echocardiography showed a significant improvement regarding post AMI remodeling as evidenced by an attenuated loss of ejection fraction and preserved ventricular geometry. Left ventricular ejection fraction (LVEF) in rats receiving supernatants from apoptotic cells evidenced a mean value of 56±4% compared to 60±5% in sham operated animals, whereas untreated or viable cell supernatant infused animals showed a significant decline of LVEF to 44±3% and 41±4% respectively (p<0.001).

These data indicate that infusion of supernatants derived from irradiated apoptotic PBMC in experimental AMI circumvented inflammation and caused preferential homing of regenerative EPC leading to preservation of ventricular function.

Methods

Cell Culture of Human PBMC for in vitro Assays

Human peripheral blood mononuclear cells (PBMC) were obtained by Ficoll density grade centrifugation as described previously. To induce apoptosis in human PBMC, cells were irradiated with 60Gy (irradiation automat for human blood products, Department of Hematology, General Hospital Vienna). Both viable and irradiated apoptotic (IA-) PBMC were incubated at 37° Celsius for 24 hours at various cell densities ($1*10^6$, $5*10^6$, $10*10^6$ and $25*10^6$ cells/milliliter, n–5). Then supernatants were obtained and levels of secreted proteins were measured by Enzyme-linked immunosorbent assay (ELISA, R&D Systems, Minneapolis, USA), according to the protocolls supplied by the manufacturer.

Acquisition of Syngeneic IA-PBMC and Viable-PBMC for AMI in vivo Experiment

Syngeneic rat PBMC for in vivo experiments were separated by density gradient centrifugation from whole-blood obtained from prior heparinized rats by puncturing of right atrium. Apoptosis was induced by Cs-137 cesium irradiation with 45Gy for in vivo experiments and cultured at 37° Celsius at a cell density of $25*10^6$ cells/milliliter). Induction of apoptosis by irradiation was measured by flow cytometry (annexin V staining >80% for IA-PBMC, annexin V staining <20% for viable PBMC). Cells were incubated for 24 hrs in a humidified atmosphere (5% CO2, 37° C., relative humidity 95%). Supernatants were removed and dialysed with a 3.5 kDa cutoff (Spectrum laboratories, Breda, The Netherlands) against 50 mM ammonium acetate overnight at 4° C. Then supernatants were sterile filtrated and lyophilized. Lyophilized secretoma were stored at −80° C. and freshly resuspended for every experiment. Secretoma were radom sampled for their pH value. The lyophilized powder was stored at −80° Celsius until further experiments were conducted.

Induction of Myocardial Infarction

Animal experiments were approved by the committee for animal research, Medical University of Vienna. All experiments were performed in accordance to the Guide for the Care and Use of Laboratory Animals by the National Institutes of Health (NTH). Myocardial infarction was induced in adult male Sprague-Dawley rats by ligating the left anterior descending artery (LAD). In short, animals were anesthetized intraperitoneally with a mixture of xylazin (1 mg/100 g bodyweight) and ketamin (10 mg/100 g bodyweight) and ventilated mechanically. A left lateral thoracotcmy was performed and a ligature using 6-0 prolene was placed around the LAD beneath the left atrium. Immediately after the onset of isohemia, lyophilized supernatants obtained from $8\times10^6$ apoptotic PBMC resuspended in 0.3 ml cell culture medium were infused over the femoral vein. Infusion of cell culture medium alone, viable PBMC supernatants and sham operation served as negative controls in this experimental setting, respectively. The experimental design is shown in FIG. 1.

Histology and Immunohistochemistry In Vivo

See example 1.

Determination of Myocardial Infarction Size by Planimetry

See example 1.

Cardiac Function Assessment by Echocardiography

See example 1.

Statistical Methods

Statistical analysis was performed using Graph Pad Prism software (USA). All data are given as mean±standard error of the mean. Paired two-sided t-tests for dependent, unpaired t-tests for independent variables were utilized calculating significances.

Between-group differences regarding survival of acute myocardial infarction were compared by Kaplan-Meier actuarial analysis. Bonferroni-Holm correction was used to adjust p-values for multiple testing. P-values <0.05 were considered statistically significant.

Results

Determination of Paracrine Factors Secreted by IA-PBMC and Viable PBMC by ELISA

The results are shown in FIGS. 10 to 15.

Example 6

Paracrine Factors Secreted by Peripheral Blood Mononuclear Cells Posses Immunesuppressive Features In Example 1 anti-inflammatory effects of PBMC secretoma in an acute myocardial infarction (AMI) animal model are evidenced. In this example it is shown that the application of PBMC secretoma after AMI induction inhibits the inflammatory damage of the heart muscle by massively down-regulating the immune response.

Based on these findings possible immunesuppressive effects of secretoma in in vitro experiments were investigated. CD4+ cells play a key role in the orchestration of the immune response as they are pivotal for the assistance of other leukocytes (e.g. macrophages, B cells, cytotoxic T cells) in immunological processes.

Material and Methods

Production of PBMC Secretoma

PBMC from healthy volunteers were separated by Ficoll density centrifugation. Cells were resuspended in Ultra Culture Medium (Lonza, Basel, Switzerland) at a concentration of $1*10^6$ cells/mL (sup liv). For the production of secretoma from apoptotic PBMC apoptosis was induced by irradiation with 60 Gy (sup APA). Cells were incubated for 24 h in a humidified atmosphere (5% CO2, 37° C., relative humidity 95%). Supernatants were removed and dialysed with a 3.5 kDa cutoff (Spectrum laboratories, Breda, The Netherlands) against 50 mM ammonium acetate overnight at 4° C. Then supernatants were sterile filtrated and lyophilized. Lyophilized secretoma were stored at −80° C. and freshly resuspended for every experiment. Secretoma were radom sampled for their pH value.

Separation of CD4 Cells

CD4+ cells were separated by depletion of non-CD4+ T cells utilizing a MACS bead system (Miltenyi, Bergisch Gladbach, Germany). Cells were freshly prepared and immediately used for each experiment.

Measurement of Apoptosis

Apoptosis was detected by flow cytometry using a commercially available Annexin V/PI kit (BD, New Jersey, USA). Apoptotis were defined by Annexin positive staining, late apoptosis by PI positivity.

Proliferation Experiments

PBMC or purified CD4+ cells were diluted in Ultra Culture supplemented with 0.2% gentamycinsulfate (Sigma, St. Louis, Mo., USA), 0.5% β-mercapto-ethanol (Sigma, St Louis, Mo., USA) and 1% GlutaMAX-I (Invitrogen, Carlsbad, Calif., USA) to a concentration of $1*10^5$/well in a 96 round-bottom well plate. Cells were stimulated with either PHA (7 µg/mL, Sigma, USA), CD3 (10 µg/mL, BD, New Jersey, USA) IL-2 (10 U/mL, BD, USA) or an 1:1 ratio of allogeneic irradiated (60 Gy) PBMC for MLR. Cells were incubated for 48 h or 5 days (MLR) with different concentrations of PBMC secretoma, IL-10 or TGF-β. Then cells were pulsed for 18 h with 3[H]-thymidine ($3.7\times10^4$ Bq/well; Amersham Pharmacia Biotech, Uppsala, Sweden). Cells were harvested and 3[H]-thymidine incorporation was measured in a liquid scintillation counter.

Activation Markers

Purified CD4+ cells were stimulated with anti-CD3 (10 µg/mL) and co-incubated with different concentration of PBMC secretoma. Cells were stained for CD69 and CD25 following a standard flow cytometric staining protocol and analyzed on a flow cytometer FC500 (Beckman Coulter, Fullerton, Calif., USA).

Results

In preliminary experiments the anti-proliferative properties of PBMC supernatants from viable cells (sup liv) were tested. In anti-CD3 and PHA stimulation experiments proliferations rates were significantly reduced by the addition of secretoma (n=10).

Based on these findings the effect of PBMC secretoma on the T-helper cell compartment was evaluated, since these cells play a pivotal role in launching and perpetuating an immune response. In analogy to FIG. 16 highly purified CD4− cells lost their proliferative capacity by the addition of secretoma. This phenomenon was observed for the supernatant of living as well as of apoptotic, irradiated PBMC (FIG. 17, n=5).

The next step was to determine possible effects of the secretoma on cell viability. Therefore resting CD4+ cells were incubated with supernatant and Annexin V and PI positivity was evaluated. Supernatants from both, living and apoptotic PBMC, evidenced remarkable pro-apoptotic effects (FIG. 18, n=5).

To test if PBMC secretoma were able to inhibit CD4+ cell activation the T cell activation markers CD25 and CD69 following anti-CD3 stimulation of CD4+ cells was evaluated. The upregulation of both markers was significantly and dose-dependent inhibited by PBMC secretoma (FIG. 19, n=5).

In a last set of experiments the effect of the immune-suppressive cytokines IL-10 and TGF-β by the addition of neutralizing antibodies in these experiments was examined. Neither IL-10 and TGF-β was found to be responsible for the anti-proliferative effects of our PBMC secretoma, since demonetizing these cytokines did not increase proliferation rates (FIG. 20, n=5).

CONCLUSION

These experiments evidence for the first time that PBMC secretoma posses immune-suppressive features in vitro. It was shown that supernatant a) reduces proliferation rates in anti-CD3, PHA and MLR stimulation experiments, b) has the potency to induce apoptosis and inhibits activation of CD4+ cells upon T cell triggering.

The invention claimed is:

1. A pharmaceutical preparation, comprising a dosage form of a cell-free culture supernatant of peripheral blood mononuclear cells (PBMCs), the cell-free culture supernatant comprising at least 2000 pg/mL of matrix metallopeptidase 9 (MMP-9) and no detectable amount of TNF-α, the PBMCs comprising non-activated, non-proliferating T cells, B cells, NK cells, and monocytes cultivated under a stress inducing condition comprising a dose of at least 10 Gy radiation in a physiological solution free of PBMC-proliferating and PBMC-activating substances for at least 1 h.

2. The pharmaceutical preparation according to claim 1, wherein the physiological solution is selected from the group consisting of a salt solution, whole blood, blood fraction, and a cell culture medium.

3. The pharmaceutical preparation according to claim 2, wherein the cell culture medium is selected from the group consisting of Roswell Park Memorial Institute Medium (RPMI), Dulbecco Modified Eagle Medium (DMEM), serum-free hematopoietic cell media and Ultraculture.

4. The pharmaceutical preparation according to claim 1, wherein the radiation comprises γ-radiation.

5. The pharmaceutical preparation according to claim 1, wherein the cell-free culture supernatant is suitable for subcutaneous administration, intramuscular administration, intra-organ administration, and intravenous administration.

6. The pharmaceutical preparation according to claim 1, wherein said cell-free culture supernatant is lyophilised.

7. The pharmaceutical preparation according to claim 1, wherein the PBMCs are cultivated in said physiological solution for at least 4 h.

8. The pharmaceutical preparation according to claim 2 wherein said salt solution is a physiological NaCl solution.

9. The pharmaceutical preparation according to claim 2 wherein said blood fraction is serum.

10. The pharmaceutical preparation according to claim 4 wherein the dose of said radiation is at least 20 Gy.

11. The pharmaceutical preparation according to claim 4 wherein the dose of said radiation is at least 40 Gy.

12. The pharmaceutical preparation according to claim 1 wherein said cultivation is for at least 6 h.

13. The pharmaceutical preparation according to claim 1 wherein said cultivation is for at least 12 h.

14. The pharmaceutical preparation according to claim 1 wherein said cultivation is for at least 24 h.

15. The pharmaceutical preparation according to claim 14 wherein said radiation is γ-radiation.

16. The pharmaceutical preparation according to claim 15 wherein the dose of said γ-radiation is at least 40 Gy.

17. The pharmaceutical preparation according to claim 15 wherein the dose of said γ-radiation is at least 60 Gy.

18. The pharmaceutical preparation according to claim 1, wherein the cell-free culture supernatant has no detectable amount of INF-γ.

19. A pharmaceutical preparation, comprising a dosage form of a culture supernatant of peripheral blood mononuclear cells (PBMCs) free of cells other than the PBMCs, the supernatant comprising at least 2000 pg/ml of matrix metallopeptidase 9 (MMP-9) and no detectable amount of TNF-α and INF-γ, wherein the PBMCs are selected from non-activated, non-proliferating T cells, B cells, NK cells, and monocytes cultivated in vitro under a stress inducing condition comprising a dose of at least 10 Gy radiation and in a physiological solution free of PBMC-proliferating and PBMC-activating substances for least 1 h, wherein the culture supernatant PBMC optionally contains PBMCs.

20. A pharmaceutical preparation, comprising a dosage form of a culture supernatant having no detectable amount of TNF-α, the culture supernatant being produced by in vitro cultivation of peripheral blood mononuclear cells (PBMCs) exposed to at least 10 Gy γ-radiation in a physiological solution free of PBMC-proliferating and PBMC-activating substances for at least 1 h, the PBMCs being separated from whole blood and consisting of T cells, B cells, NK cells, and monocytes.

* * * * *

UNITED STATES PATENT AND TRADEMARK OFFICE
CERTIFICATE OF CORRECTION

PATENT NO.         : 10,478,456 B2
APPLICATION NO.    : 13/140120
DATED              : November 19, 2019
INVENTOR(S)        : Hendrik Jan Ankersmit It is certified that error appears in the above-identified patent and that said Letters Patent is hereby corrected as shown below:

In the Specification

Column 3
Line 12, change "PBMC" to –PBMCs–
Line 24, change "were" to –that were–

Column 4
Lines 2-3, change "shows Kaplan-Meier" to –shows the Kaplan-Meier–
Line 36, change "cultivating them" to –cultivation–
Line 61, change "prior their" to –prior to their–

Column 5
Line 13, change "interchangeable" to –interchangeably–
Line 52, change "integrety" to –integrity–

Column 6
Line 6, change "infarct" to –infarction–

Column 8
Line 49, change "PBMC" to –PBMCs–

Column 9
Line 5, change "immunchistogical" to –immunohistological–

Column 10
Line 35, change "infracted" to –infarcted–
Line 36, change "component" to –components–

Column 13
Line 23, remove [or]

Signed and Sealed this
Fourth Day of February, 2020

Andrei Iancu
*Director of the United States Patent and Trademark Office*

Line 54, change "a" to –an–

Column 16
Line 40, change "a" to –an–

Column 18
Line 60, change "asterix" to –asterisks–
Line 65, change "asterix" to –asterisks–

Column 21
Line 47, change "radom" to –random–

Column 22
Line 62, change "radom" to –random–

Column 23
Line 15, change "an" to –a–

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctgatgag atcgagtaca tctt                                           24

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accgcctcgg cttgtcac                                                  18

<210> SEQ ID NO 3
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 3
ctcttggcag ccttcctgat t                                           21

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tatgcactga catctaagtt ctttagca                                    28

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggaagatgc tggtgttca                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctggcagaa ataggcttc                                              19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgagtatg cctgccgtgt g                                           21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caatccaaat gcggcatct                                              19
```